United States Patent
Shigemori

(10) Patent No.: US 8,382,658 B2
(45) Date of Patent: Feb. 26, 2013

(54) CAPSULE ENDOSCOPE SYSTEM

(75) Inventor: Toshiaki Shigemori, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 807 days.

(21) Appl. No.: 12/546,093

(22) Filed: Aug. 24, 2009

(65) Prior Publication Data

US 2009/0312601 A1 Dec. 17, 2009

Related U.S. Application Data

(63) Continuation of application No. PCT/JP2008/053186, filed on Feb. 25, 2008.

(30) Foreign Application Priority Data

Feb. 26, 2007 (JP) .................. 2007-046012

(51) Int. Cl.
*A61B 1/00* (2006.01)
(52) U.S. Cl. ...................................... 600/103
(58) Field of Classification Search .................. 600/103, 600/117–118
See application file for complete search history.

(56) References Cited

U.S. PATENT DOCUMENTS

| 2009/0131746 A1* | 5/2009 | Seo et al. ...................... 600/101 |
| 2009/0240108 A1* | 9/2009 | Shimizu et al. ............... 600/109 |

FOREIGN PATENT DOCUMENTS

| JP | 2002-272822 | 9/2002 |
| JP | 2003-019111 | 1/2003 |
| JP | 2004-313242 | 11/2004 |
| JP | 2005-348928 | 12/2005 |

* cited by examiner

*Primary Examiner* — Christopher Mahoney
(74) *Attorney, Agent, or Firm* — Scully Scott Murphy & Presser, PC

(57) ABSTRACT

A capsule endoscope system includes: a receiving device that receives in-vivo images captured by a capsule endoscope inserted into an organ of a subject; and an image display device that acquires ID information of one or more capsule endoscopes, acquires through the receiving device the in-vivo images captured by the capsule endoscopes identified by the ID information, and displays thereon the in-vivo images thus acquired. The image display device is connected via a communication network to a central server that uniformly manages information about the capsule endoscopes, notifies the central server the ID information of the one or more capsule endoscopes, acquires information about the one or more capsule endoscopes from the central server, and performs a warning process about the one or more capsule endoscopes according to the information thus acquired.

12 Claims, 12 Drawing Sheets

FIG.8

CAPSULE ENDOSCOPE SYSTEM

CROSS-REFERENCE TO RELATED APPLICATIONS

This application is a continuation of PCT international application Ser. No. PCT/JP2008/053186 filed on Feb. 25, 2008 which designates the United States, incorporated herein by reference, and which claims the benefit of priority from Japanese Patent Application No. 2007-046012, filed on Feb. 26, 2007, incorporated herein by reference.

BACKGROUND OF THE INVENTION

1. Field of the Invention

The present invention relates to a capsule endoscope system in which a capsule endoscope is inserted into an organ of a subject, such as a patient, to acquire image data of the inside of the subject.

2. Description of the Related Art

In recent years, in the field of endoscopes, capsule endoscopes having imaging function and wireless communication function have appeared. A capsule endoscope system is proposed in which images of the inside of organs of a subject are captured with such a capsule endoscope, the images are successively received by a receiving device, the images of inside of the subject received thereby are successively displayed by a image display device such as a workstation, and thus, the inside the body of the subject are observed (examined).

In such a capsule endoscope system, a capsule endoscope is swallowed from the mouth of a subject, such as a patient, for observation (examination). While traveling through the inside of organs such as the stomach and the small intestine due to the peristaltic motion until the endoscope is naturally excreted, the endoscope successively captures images of the inside of organs (hereinafter, also referred to as in-vivo images) of the subject at predetermined intervals. The capsule endoscope wirelessly transmits the in-vivo images successively to a receiving device that is carried by the subject (see Japanese Patent Application Laid-open No. 2003-19111).

The in-vivo images transmitted by the capsule endoscope are successively received by the receiving device carried by the subject, and successively stored in a storage medium in the receiving device. Then, the storage medium in which the in-vivo images are stored is detached from the receiving device and inserted into a display device, such as a workstation. The display device acquires the in-vivo images of the subject via the storage medium and displays on a display the in-vivo images of the subject thus acquired. Users, such as a doctor and a nurse, successively observe the in-vivo images displayed on the image display device and diagnose the subject.

SUMMARY OF THE INVENTION

A capsule endoscope system according to an aspect of the present invention includes: a receiving device that receives in-vivo images captured by a capsule endoscope inserted into an organ of a subject; and an image display device that acquires ID information of one or more capsule endoscopes, acquires through the receiving device the in-vivo images captured by the capsule endoscopes identified by the ID information, and displays thereon the in-vivo images thus acquired, wherein the image display device is connected via a communication network to a central server that uniformly manages information about the capsule endoscopes, notifies the central server the ID information of the one or more capsule endoscopes, acquires information about the one or more capsule endoscopes from the central server, and performs a warning process about the one or more capsule endoscopes according to the information thus acquired.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 8 is a schematic diagram showing an example of a window for preparing a diagnostic report of the subject;

DETAILED DESCRIPTION OF THE PREFERRED EMBODIMENTS

Exemplary embodiments of a capsule endoscope system according to the present invention are described below in detail with reference to the accompanying drawings. The present invention is, however, not limited thereto.

First Embodiment

Figure 1:
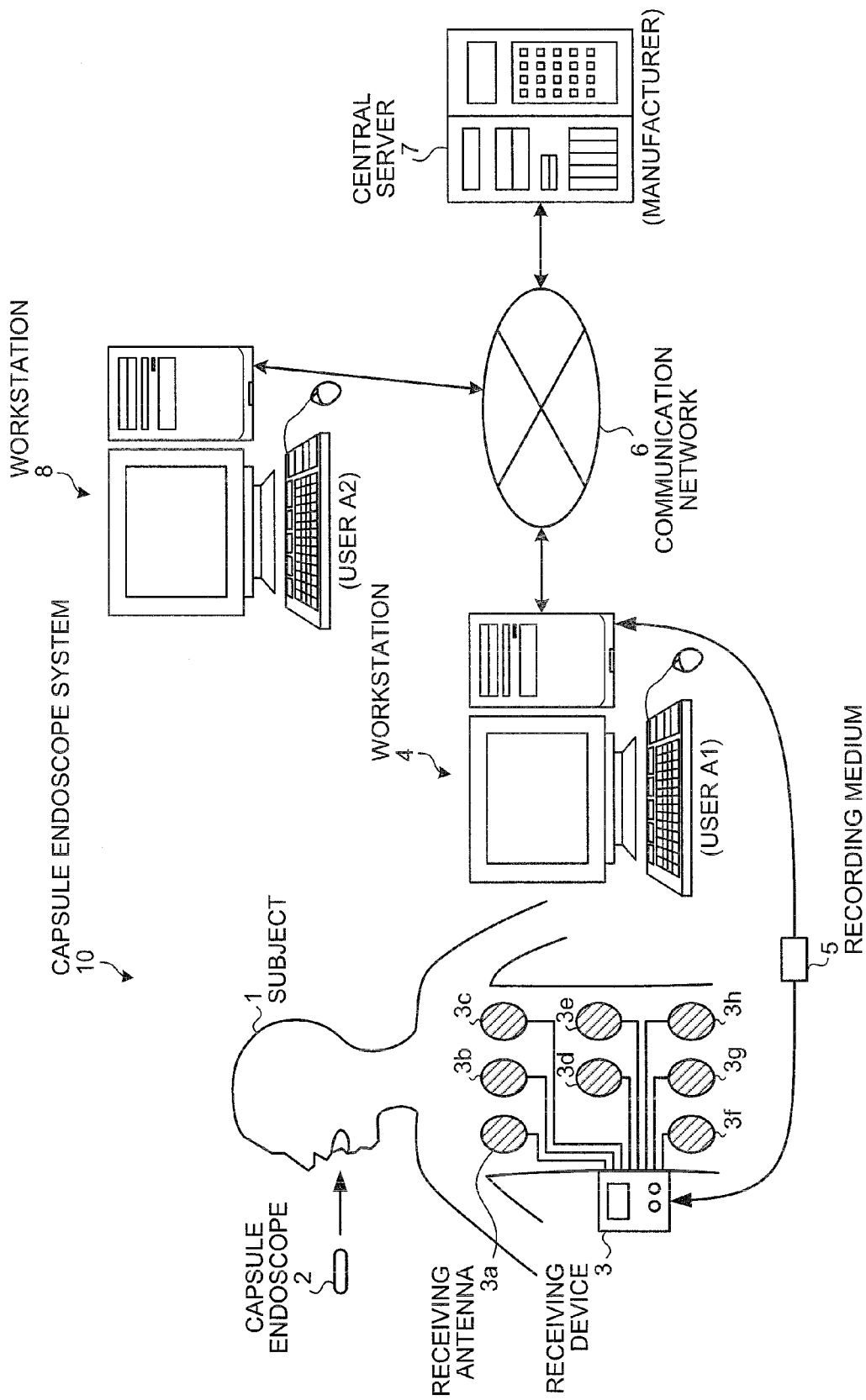
FIG. 1 is a schematic diagram showing a configuration example of a capsule endoscope system according to a first embodiment of the present invention.

FIG. 1 is a schematic diagram showing a configuration example of a capsule endoscope system according to a first embodiment of the present invention. As shown in FIG. 1, a capsule endoscope system 10 according to the first embodiment includes a capsule endoscope 2 that captures in-vivo images of a subject 1 such as a patient, a receiving device 3 that receives the in-vivo images of the subject 1 from the capsule endoscope 2, a workstation 4 that displays the in-vivo images (that is, the in-vivo images captured by the capsule endoscope 2) of the subject 1 received by the receiving device 3, and a portable recording medium 5 that is used for exchanging data between the receiving device 3 and the workstation 4. The capsule endoscope in the capsule endoscope system 10 is thrown away after being used once for examining the subject. Although not particularly shown, one or more capsule endoscopes are used in the capsule endoscope system 10. The one or more capsule endoscopes include the capsule endoscope 2 to be inserted into the subject 1 as shown in FIG. 1 and have the functions similar to that of the capsule endoscope 2.

The capsule endoscope 2, which is used for capturing the in-vivo images of the subject 1, includes imaging function and wireless communication function within a capsule shaped casing that can be inserted into the organs of the subject 1. More specifically, the capsule endoscope 2 is swallowed from the mouth of the subject 1, and then, successively captures in-vivo images at predetermined intervals (for example, 0.5-second intervals) while traveling through organs of the subject 1 due to, for example, the peristaltic motion of organs. The capsule endoscope 2 wirelessly transmits an image signal including the in-vivo images of the subject 1 successively to the external receiving device 3. The capsule endoscope 2 has ID information to identify the capsule endoscope 2 itself (hereinafter, "capsule ID"), and adds the capsule ID to the image signal including image data captured thereby. The capsule endoscope 2 wirelessly transmits the capsule ID of the capsule endoscope 2 as well as the image data such as the in-vivo images successively to the external receiving device 3.

The receiving device 3 is used for receiving the in-vivo images of the subject 1 captured by the capsule endoscope 2. More specifically, the receiving device 3, which has plural receiving antennas 3*a* to 3*h*, is placed on (carried by) the subject 1 of which the capsule endoscope 2 is inserted into the organs. The receiving device 3 successively receives image signals wirelessly transmitted by the capsule endoscope 2 through the receiving antennas 3*a* to 3*h*, and then, acquires image data contained in the image signals (image data of, for example, in-vivo images captured by the capsule endoscope 2) and the capsule ID of the capsule endoscope 2 that are contained in the image signals. The receiving device 3, which has the recording medium 5, stores in the recording medium 5 the in-vivo images of the subject 1 and the capsule ID of the capsule endoscope 2 that are received from the capsule endoscope 2.

The receiving antennas 3*a* to 3*h* are, for example, dispersively arranged on the body surface of the subject 1 along the traveling path of the capsule endoscope 2 (that is, the alimentary tract of the subject 1), and are connected to the receiving device 3. The receiving antennas 3*a* to 3*h* capture the image signals wirelessly transmitted successively by the capsule endoscope 2, which is inside an organ of the subject 1, and successively sends out the image signals captured thereby to the receiving device 3. The receiving antennas 3*a* to 3*h* may be dispersively arranged on, for example, a jacket that is worn by the subject 1. One or more receiving antennas that capture the image signals from the capsule endoscope 2 may be arranged on the subject 1, and the number of the receiving antennas is not limited to eight.

The workstation 4, which acquires various data such as the in-vivo images of the subject 1 through the recording medium 5, has a function as an image display device that displays, on a display screen, the various data acquired thereby. The workstation 4 displays thereon the in-vivo images of the subject 1 acquired through the recording medium 5. A user such as a doctor and a nurse observes (examines) the in-vivo images of the subject 1 displayed by the workstation 4 and diagnoses the subject 1. The workstation 4 has a report creating function by which a diagnostic report in which a diagnostic result and the like for the subject 1 are described is created. The workstation 4 displays the diagnostic report on a display.

The workstation 4 acquires the capsule IDs of one or more capsule endoscopes used in the capsule endoscope system 10 (for example, the capsule endoscope 2 inserted into the organs of the subject 1) and the image data, and holds and manages the capsule IDs in association with the image data acquired from the one or more capsule endoscopes. For example, the workstation 4 acquires the in-vivo images of the subject 1 and the capsule ID of the capsule endoscope 2 through the recording medium 5, and then, holds and manages the capsule ID in association with the in-vivo images of the subject 1 that are acquired thereby. The workstation 4 is connected, via a communication network 6, to a central server 7 that uniformly manages various pieces of information about the capsule endoscopes, and transmits and receives various pieces of information about the one or more capsule endoscopes used in the capsule endoscope system 10 to and from the central server 7. The workstation 4 notifies the central server 7, via the communication network 6, of one or more capsule IDs that the workstation 4 holds and manages, and acquires, from the central server 7, various pieces of information about the one or more capsule endoscopes identified by the notified one or more capsule IDs. The workstation 4 holds and manages the information (various pieces of information about one or more capsule endoscopes) associated with the capsule IDs acquired from the central server 7, and performs a warning process about one or more capsule endoscopes used in the capsule endoscope system 10 according to the various pieces of information about the one or more capsule endoscopes.

The recording medium 5, which is a portable recording medium, is used for exchanging data between the receiving device 3 and the workstation 4. More specifically, the recording medium 5 is attachable to and detachable from the receiving device 3 and the workstation 4 and can output and record data thereto when the recording medium 5 is inserted thereinto. The recording medium 5 records therein the in-vivo images and the like of the subject 1 that the receiving device 3 receives from the capsule endoscope 2 when the recording medium 5 is inserted into the receiving device 3, and sends out, to the workstation 4, recorded data such as the in-vivo images of the subject 1 when the recording medium 5 is inserted into the workstation 4.

Various data that the recording medium 5 records therein includes, for example, the in-vivo images of the subject 1, time information (imaging time, receiving time, and the like) of each in-vivo image included in the in-vivo images, the capsule ID of the capsule endoscope 2 that has captured the in-vivo images of the subject 1, patient information of the subject 1, and examination information about the subject 1. Here, the patient information of the subject 1, which is the information identifying the subject 1, is, for example, the patient name, the patient ID, the date of birth, the sex, and the age of the subject 1. The examination information of the subject 1, which is information identifying a capsule endoscope examination (examination for observing the inside of an organ by inserting the capsule endoscope 2 into the organ) performed on the subject 1, includes, for example, the examination ID and the examination date.

The central server 7 functions as an information management server that uniformly manages various pieces of information about plural capsule endoscopes each used in plural capsule endoscope systems. More specifically, as shown in FIG. 1, the central server 7, for example, an information management server that belongs to a capsule endoscope manufacturer, is connected via the communication network 6 to workstations 4 and 8 of capsule endoscope systems for plural users A1 and A2. The central server 7 uniformly manages various pieces of information, such as manufacturing history information about the capsule endoscope used in capsule endoscope systems for the users A1 and A2. The manufacturing history information of each capsule endoscope includes information of component parts thereof and the like, the manufacturing LOT number, the manufacturing date, and the manufacturing location thereof. The central server 7 registers therein the capsule IDs of the capsule endoscopes notified by the workstations 4 and 8. The central server 7 transmits (provides), to the workstations 4 and 8 that hold and manage the registered capsule IDs, various pieces of information such as manufacturing history information of each capsule endoscope identified by each registered capsule ID (for example, the capsule endoscope 2). Besides the manufacturing history information, various pieces of information provided by the central server 7 may include, for example, information such as error information indicating that the error has occurred in a capsule endoscope in which a battery is exhausted (or may exhaust) even though the capsule endoscope is within expiration date of validity (expiration date for use) and the capsule ID of such capsule endoscope.

The workstation 8 shown in FIG. 1 is a workstation (not shown) in a capsule endoscope system that belongs to a user A2 who is a user different from the user A1 of the capsule endoscope system 10. The workstations 4 and 8 have functions that are generally similar to each other. The communication network 6 is formed of the Internet, an Intranet, a wired LAN, a wireless LAN, or the like.

Figure 2:
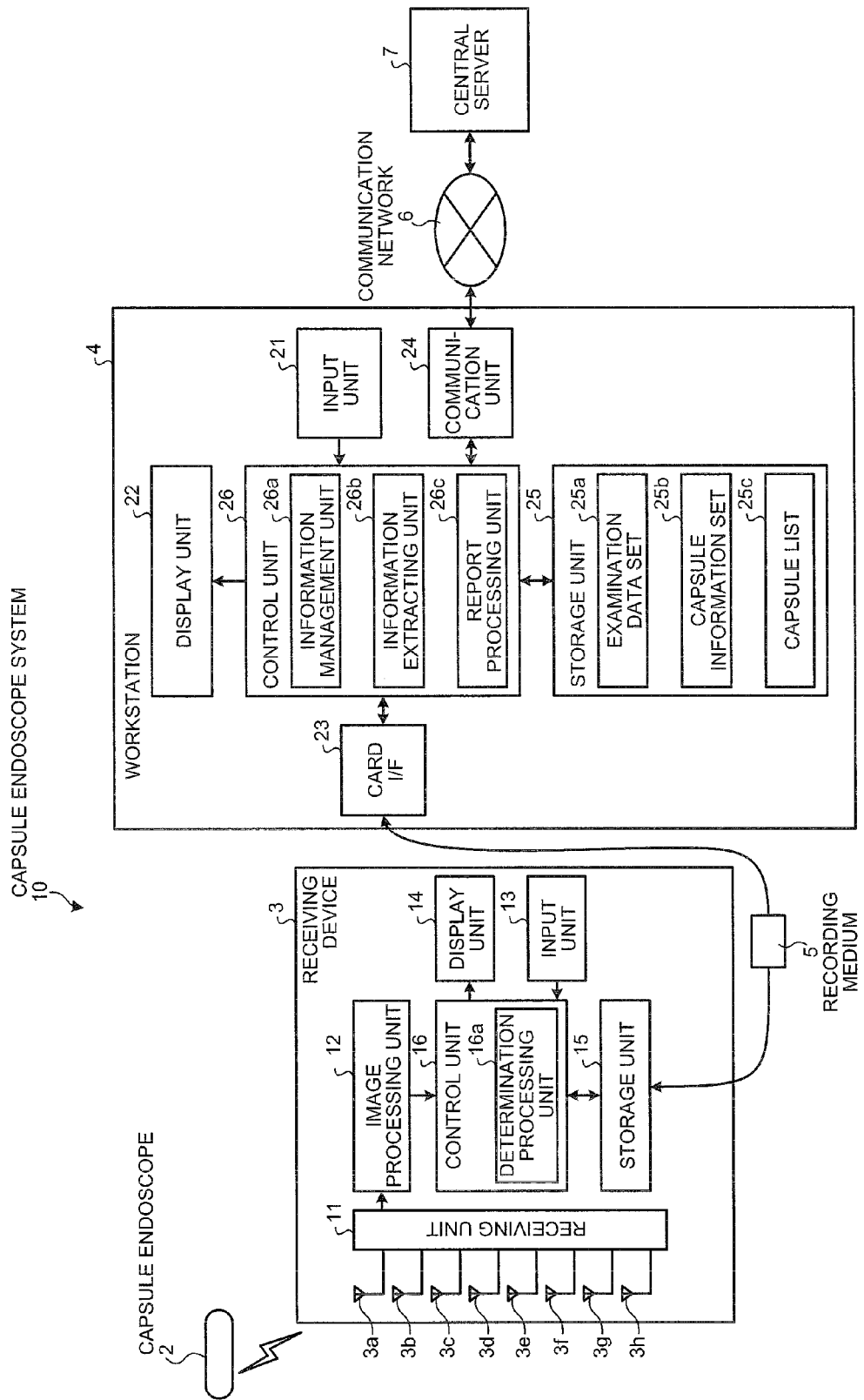
FIG. 2 is a block diagram schematically showing a configuration example of the capsule endoscope system according to the first embodiment.

Configurations of the receiving device 3 and the workstation 4 of the capsule endoscope system 10 according to the first embodiment of the present invention are described below in detail. FIG. 2 is a block diagram schematically showing a configuration example of the capsule endoscope system according to the first embodiment of the present invention. A configuration of the receiving device 3, and then, of the workstation 4 are described below in detail with reference to FIG. 2.

The receiving device 3 includes a receiving unit 11 that receives an image signal wirelessly transmitted by the capsule endoscope 2, an image processing unit 12 that creates an in-vivo image of the subject 1 according to the image signal, an input unit 13 including plural input buttons, a display unit 14 such as a liquid crystal display, a storage unit 15 into which the recording medium 5 is inserted, and a control unit 16 that controls the units of the receiving device 3.

The receiving unit 11, to which the receiving antennas 3a to 3h are connected, receives an image signal from the capsule endoscope 2 through the receiving antennas 3a to 3h. Here, the receiving unit 11 selects the antenna having the highest receiving electric field intensity from the receiving antennas 3a to 3h, and receives a wireless signal from the capsule endoscope through the receiving antenna thus selected. The receiving unit 11 provides the received wireless signal with a predetermined receiving process such as a demodulation process, thereby demodulating the wireless signal into an image signal. The image signal demodulated by the receiving unit 11 includes the image data captured by the capsule endoscope 2 (for example, the in-vivo images of the subject 1) and the capsule ID of the capsule endoscope 2. That is, the receiving unit 11 simultaneously receives the image data captured by the capsule endoscope 2 and the capsule ID of the capsule endoscope 2. The receiving unit 11 transmits, to the image processing unit 12, the image signal including the image data and the capsule ID.

The image processing unit 12 acquires the image signal from the receiving unit 11, and provides the image signal with a predetermined image processing to create an in-vivo image of the subject 1 captured by the capsule endoscope 2. The image processing unit 12 extracts the capsule ID of the capsule endoscope 2 contained in the image signal acquired from the receiving unit 11, and transmits, to the control unit 16, the capsule ID thus extracted and the in-vivo image of the subject 1 thus created.

The input unit 13, which is formed using plural input buttons, inputs to the control unit 16, instruction information to give an instruction to the control unit 16. The display unit 14, which is formed using a liquid crystal display and the like, displays thereon the information that the control unit 16 instructs to display. The storage unit 15, into which the recording medium 5 can be detachably inserted, functions as a storage unit of the receiving device 3 when the recording medium 5 is inserted into the storage unit 15. The storage unit 15 stores, in the recording medium 5, various pieces of information such as the in-vivo images of the subject 1 and the capsule ID of the capsule endoscope 2, according to control performed by the control unit 16.

The control unit 16 controls the units of the receiving device 3 (that is, the receiving unit 11, the image processing unit 12, the input unit 13, the display unit 14, and the storage unit 15), to control input and output of signals therebetween. More specifically, the control unit 16 instructs the receiving unit 11 to receive the image signal from the capsule endoscope 2 according to the instruction information input by the input unit 13, instructs the image processing unit 12 to create an in-vivo image of the subject 1 according to the image signal, and instructs the display unit 14 to display information such as information indicating a receiving state of the image signal. The control unit 16 acquires the in-vivo images of the subject 1 and the capsule ID of the capsule endoscope 2, and then, associate the in-vivo images with the capsule ID. The control unit 16 controls the storage unit 15 so that the in-vivo images of the subject 1 associated with the capsule IDs are stored in the recording medium 5.

The control unit 16 determines whether the capsule endoscope 2 to be inserted into an organ of the subject 1 is an error capsule. If the capsule endoscope 2 is determined to be an error capsule, the control unit 16 instructs the display unit 14 to display warning information to warn externally that the capsule endoscope 2 is an error capsule. The control unit 16 has a determination processing unit 16a that determines whether the capsule endoscope 2 is an error capsule. Here, the error capsule means a capsule endoscope identified by error information. For example, the error capsule may be a capsule endoscope in which a battery is exhausted (or may exhaust) even though the capsule endoscope is within expiration date of validity (expiration date for use).

The determination processing unit 16a acquires an error capsule list prepared by the workstation 4 through the recording medium 5, and acquires, from the image processing unit 12, the capsule ID of the capsule endoscope 2 that is to be inserted into an organ of the subject 1. Here, the capsule IDs of one or more error capsules are listed in the error capsule list. The determination processing unit 16a checks the capsule ID of the capsule endoscope 2 against the capsule IDs listed in the error capsule list and determines whether the capsule endoscope 2 is an error capsule according to a check result thus acquired. More specifically, the determination processing unit 16a determines that the capsule endoscope 2 is normal if none of the capsule IDs listed in the error capsule list matches the capsule ID of the capsule endoscope 2. The determination processing unit 16a determines that the capsule endoscope 2 is an error capsule if any of the capsule IDs listed in the error capsule list matches the capsule ID of the capsule endoscope 2. If the determination processing unit 16a determines that the capsule endoscope 2 is an error capsule, the control unit 16 instructs the display unit 14 to display thereon, error information indicating that the use of the capsule endoscope 2 that is an error capsule is prohibited.

Configuration of the workstation 4 is described below in detail. The workstation 4 includes an input unit 21 that is used to input various pieces of information, a display unit 22 on which the in-vivo images of the subject 1 are displayed, and a card interface (I/F) 23 into which the recording medium 5 is inserted. The workstation 4 also includes a communication unit 24 that performs information communication with the central server 7 via the communication network 6, a storage unit 25 that stores therein various data such as the in-vivo images of the subject 1 and the capsule IDs, and a control unit 26 that controls the units in the workstation 4.

The input unit 21 is formed using input devices such as a keyboard and a mouse. The input unit 21 inputs various pieces of information to the control unit 26 according to the input operation performed by the user. Various pieces of information that are input to the control unit 26 with the input unit 21 are, for example, instruction information to give an instruction to the control unit 26, patient information of the subject 1, examination information of the subject 1, and the capsule IDs of one or more capsule endoscopes used in the capsule endoscope system 10. The input unit 21 functions as an information acquiring unit that acquires a capsule ID when the input unit 21 is used to input a capsule ID to the control unit 26.

The display unit 22, which is formed using various types of displays such as a CRT display or a liquid crystal display, displays thereon various pieces of information that the control unit 26 instructs to display. Here, the display unit 22 displays thereon, for example, the in-vivo images of the subject 1 captured by the capsule endoscope 2, the capsule IDs of one or more capsule endoscopes, patient information of the subject 1, examination information of the subject 1, and a diagnostic report of the subject 1. The display unit 22 also displays information about a capsule endoscope (such as error information and history information) acquired from the central server 7 via the communication network 6. The display unit 22 also displays thereon various pieces of warning information according to error information acquired from the central server.

The card I/F 23, into which the recording medium 5 is detachably inserted, performs input and output of data between the recording medium 5 that is inserted into the card I/F 23 and the control unit 26. More specifically, the card I/F 23 reads from the recording medium 5, data (such as the in-vivo images of the subject 1, time information of each in-vivo image, the capsule ID of the capsule endoscope 2, and patient information and examination information of the subject 1) recorded in the recording medium 5 that is inserted into the card I/F 23, and then, sends out to the control unit 26, the recorded data thus read. The card I/F 23 writes in the recording medium 5, various data (such as the error capsule list, patient information of the subject 1, and examination information thereof) that the control unit 26 instructs to write in the recording medium 5. When the capsule IDs read from the recording medium 5 are sent out to the control unit 26, the card I/F 23 functions as an information acquiring unit that acquires the capsule IDs.

The communication unit 24, which is connected to the central server 7 via the communication network 6, performs information communication with the central server 7. More specifically, the communication unit 24 transmits, to the central server 7, one or more capsule IDs that the control unit 26 instructs to transmit thereto, thereby notifying the central server 7 of the capsule IDs. The communication unit 24 receives from the central server 7, via the communication network 6, various pieces of information about the capsule endoscopes (such as error information and manufacturing history of one or more capsule endoscopes) specified by one or more capsule IDs of which the central server 7 is notified (that is, registered in the central server 7). The communication unit 24 sends out to the control unit 26, the various pieces of information about the capsule endoscopes acquired from the central server 7.

The storage unit 25 is formed using various types of storage media that can rewritably store data therein such as a RAM, an EEPROM, a flash memory, and a hard disk. The storage unit 25, which stores therein various data that the control unit 26 instructs to store therein, sends out to the control unit 26 the data that the control unit 26 instructs to read among the various data stored therein. The storage unit 25 stores therein an examination data set of plural subjects, a capsule information set 25b including various pieces of information about the capsule endoscopes, and a capsule list 25c in which the capsule IDs of unused capsule endoscopes are listed. A case datum of a subject (for example, the subject 1) included in the examination data set includes the in-vivo images, patient information, and examination information of the subject, time information of each in-vivo image, diagnostic report information, and the like. The case datum of each subject in the examination data set is associated with the capsule ID of the capsule endoscope that captures the in-vivo images. Meanwhile, the capsule information set 25b includes, as information about one or more capsule endoscopes, information such as the capsule IDs of one or more capsule endoscopes used in the capsule endoscope system 10, and error information and manufacturing history information acquired from the central server 7.

The storage unit 25 may be formed using drives, into which portable recording media can be detachably inserted such as a flexible disk (FD), a compact disk (CD), and a digital versatile disk (DVD), and that read or write various data from or in a recording medium inserted thereinto.

The control unit 26, which controls the units in the workstation 4 (that is, the input unit 21, the display unit 22, the card I/F 23, the communication unit 24, and the storage unit 25), controls input and output of signals between the units. More specifically, the control unit 26 controls the card I/F 23 to acquire data recorded in the recording medium 5, stores in the storage unit 25 the capsule IDs among the recorded data thus acquired as a part of the capsule information set 25b, and stores in the storage unit 25 the rest of the recorded data (such as the in-vivo images, the patient information and the examination information of the subject, and time information) as a part of the examination data set. The control unit 26, which controls the communication unit 24 to acquire various pieces of information about the capsule endoscopes (such as error information and manufacturing history information) from the central server 7, stores in the storage unit 25 the various pieces of information thus acquired as a part of the capsule information set 25b. Here, the control unit 26 may instruct the display unit 22 to display thereon the various pieces of information (such as the error information and the manufacturing history information) acquired from the central server 7. The control unit 26 instructs the display unit 22 to display thereon one or more warning information about the capsule endoscopes according to the error information. The warning information about the capsule endoscopes may be, for example, warning information that indicates that the use of a capsule endoscope identified by the error information (that is, an error capsule) is prohibited or warning information that induce revision of a case datum including the in-vivo images captured by the error capsule.

The control unit 26 reads a case datum of a desired subject from the examination data set according to the instruction information input by using the input unit 21 and instructs the display unit 22 to display thereon the in-vivo images of the subject included in the case datum thus readout. Further, the control unit 26 controls the communication unit 24 to transmit (notify) to the central server 7, one or more capsule IDs input by using the input unit 21 or one or more capsule IDs acquired with the image data through the recording medium 5 in the card I/F 23.

The control unit 26 includes an information management unit 26a, an information extracting unit 26b, and a report processing unit 26c. The information management unit 26a manages various pieces of information such as the capsule IDs, error information, and manufacturing history information of the capsule endoscopes. Here, the information management unit 26a acquires one or more capsule IDs input with the input unit 21 or one or more capsule IDs read from the recording medium 5 in the card I/F 23, and then, associates one or more capsule IDs thus acquired with various pieces of information in the capsule information set 25b (such as the error information and the manufacturing history information). The information management unit 26a manages the error information and the manufacturing history information in the capsule information set 25b for each capsule ID. The information management unit 26a associates one or more capsule IDs with data in the examination data set (the in-vivo images, the patient information, examination information, and the diagnostic report information of each subject), and manages the data in the examination data set for each capsule ID. The information management unit 26a creates a data table in which, for example, the various data in the examination data set and the various pieces of information in the capsule information set 25b are associated with the capsule IDs, and thus, holds and manages the various data in the examination data set and the various pieces of information in the capsule information set 25b with the data table.

The information management unit 26a extracts the capsule IDs of the unused capsule endoscopes from the capsule IDs managed as a part of the capsule information set 25b, and then, creates the capsule list 25c in which the capsule IDs of the unused capsule endoscopes are listed. Here, an unused capsule endoscope means a capsule endoscope that is not used in capsule endoscope examination (that is, a capsule endoscope that has not been inserted into an organ of a subject) among the capsule endoscopes that belong to the capsule endoscope system 10 (for example, the capsule endoscope 2). The information management unit 26a determines that a capsule ID that is associated with a case datum of a subject is a capsule ID of a used capsule endoscope, and that a capsule ID that is not associated with a case datum of a subject is a capsule ID of an unused capsule endoscope.

The information management unit 26a creates an error capsule list in which the capsule IDs of one or more error capsules identified by the error information are listed by controlling the communication unit 24 according to the error information acquired from the central server 7. The control unit 26 controls the card I/F 23 so that the error capsule list created by the information management unit 26a is recorded in the recording medium 5.

The information extracting unit 26b extracts the data that are associated with the capsule IDs by the information management unit 26a from the examination data set or extracts pieces of information that are associated with the capsule IDs by the information management unit 26a from the capsule information set 25b. More specifically, the information extracting unit 26b extracts the examination data of the subjects associated with the capsule IDs input with the input unit 21 from the examination data set according to the capsule IDs. The information extracting unit 26b extracts the pieces of error information or of manufacturing history information that are associated with the capsule IDs from the capsule information set 25b. The control unit 26 instructs the display unit 22 to display thereon the examination data of the subjects (such as the in-vivo images and the report information) or the capsule information set (the error information and the manufacturing history information) that are extracted by the information extracting unit 26b.

The report processing unit 26c functions as a report creating unit that creates a diagnostic report for a subject according to information such as the examination data of the subject selected from the examination data set. The report processing unit 26c prepares a diagnostic report that includes, for example, the in-vivo images of the subject 1, the capsule ID of the capsule endoscope that have captured the in-vivo images of the subject 1, the patient information of the subject 1, and the diagnostic result of the subject 1. Here, the report processing unit 26c can select whether the capsule ID of the capsule endoscope 2, the patient information of the subject 1, and the like are to be included in the diagnostic report, according to the instruction information input with the input unit 21.

Figure 3:
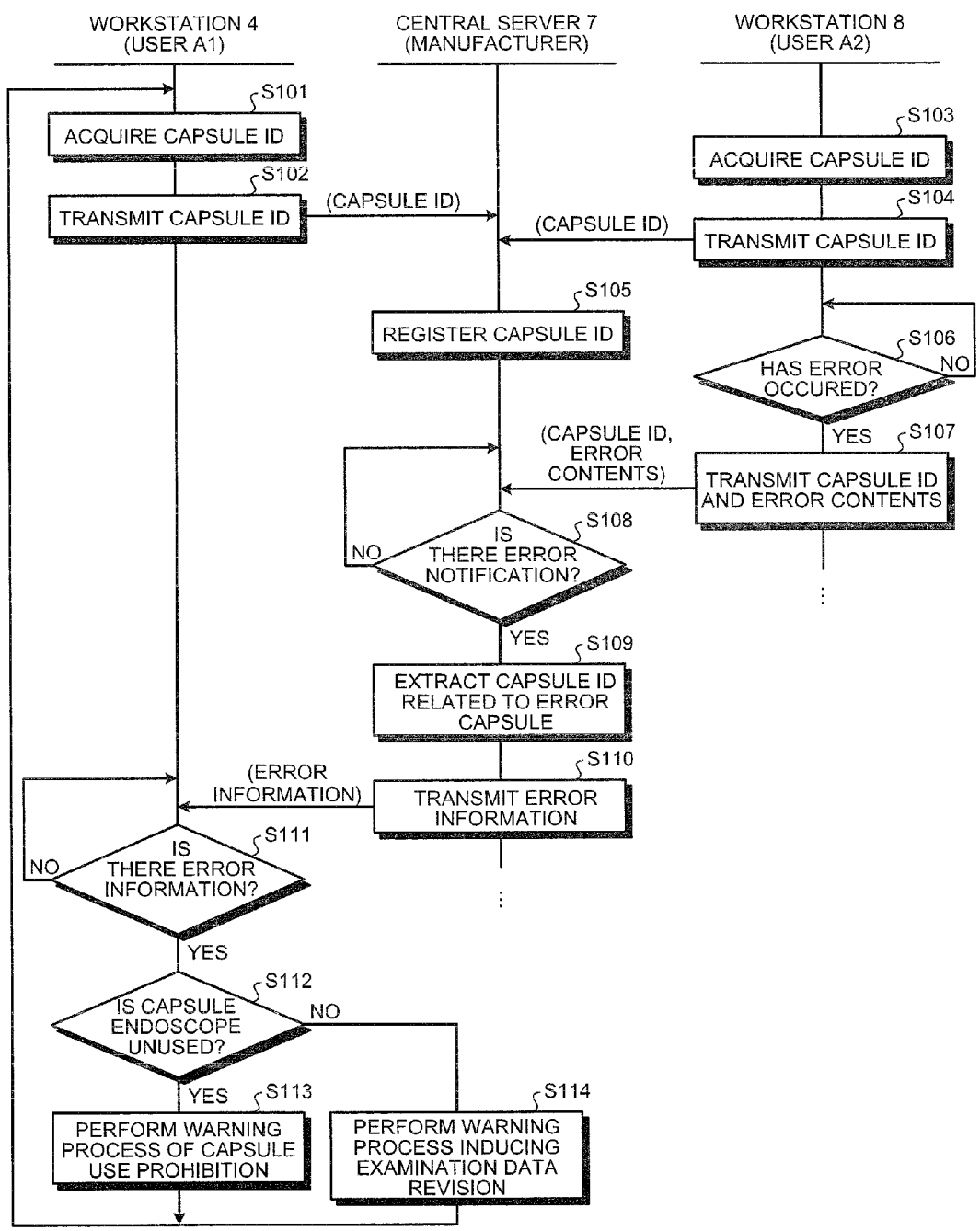
FIG. 3 is a sequence diagram showing an example of procedures performed by a workstation that performs a warning process about an error of a capsule endoscope.

Procedures performed by the workstation 4 in the capsule endoscope system 10 according to the first embodiment of the present invention are described below in detail. FIG. 3 is a sequence diagram showing an example of procedures performed by the workstation 4 that performs a warning process about an error of the capsule endoscopes. With an exemplary case in which the workstation 8 (see FIG. 1) notifies the central server 7 of the error contents of a capsule endoscope occurring in the capsule endoscope system belonging to the user A2, procedures performed by the workstation 4 that performs a warning process about error of the capsule endoscopes according to the error information acquired from the central server 7 are described below in detail.

As shown in FIG. 3, the workstation 4 acquires the capsule ID of the capsule endoscope 2 used in the capsule endoscope system 10 (Step S101), and then, transmits to the central server 7 the acquired capsule ID via the communication network 6 (Step S102). Here, the input unit 21 inputs the capsule ID of the capsule endoscope 2 to the control unit 26 by input operation. The control unit 26 acquires the capsule ID input with the input unit 21, and holds and manages the capsule ID thus acquired as a part of the capsule information set 25b. The control unit 26 controls the communication unit 24 to transmit the capsule ID thus acquired to the central server 7. Here, the communication unit 24 transmits the capsule ID to the central server 7 via the communication network 6.

In the meantime, in the way generally similar to the workstation 4 belonging to the user A1, the workstation 8 acquires the capsule ID of the capsule endoscope used in the capsule endoscope system belonging to the user A2 (Step S103), and transmits the acquired capsule ID to the central server 7 via the communication network 6 (Step S104).

The central server 7 successively receives the capsule IDs from the workstations 4 and 8, and successively registers therein the capsule IDs from the workstations 4 and 8 (Step S105). Although not specifically shown in FIG. 3, the central server 7 may transmit to the workstation 4, the manufacturing history information of the capsule endoscope identified by the capsule ID notified by the workstation 4. Similarly, the central server 7 may transmit to the workstation 8, the manufacturing history information of the capsule endoscope identified by the capsule ID notified by the workstation 8.

Meanwhile, if an error of the capsule endoscope occurs in the capsule endoscope system belonging to the user A2 after the capsule ID is transmitted to the central server 7 (Yes at Step S106), the workstation 8 belonging to the user A2 acquires the error contents and the capsule ID of the capsule endoscope in which an error has occurred (that is, an error capsule). The workstation 8 transmits to the central server 7 via the communication network 6, the error contents and the capsule ID of the error capsule thus acquired (Step S107).

If an error of the capsule endoscope does not occur in the capsule endoscope system belonging to the user A2 (No at Step S106), information such as the error contents of the error capsule is not input to the workstation 8, and thus, the workstation 8 waits for the input of various information about the capsule endoscope (such as the error contents and the capsule ID) or various data including in-vivo images of the subject.

Meanwhile, the central server 7 holds and manages the various pieces of information (such as the capsule IDs and the manufacturing history information) after registering the capsule IDs at Step S105, and determines whether an error about the capsule endoscopes has been notified (Step S108). If the central server 7 receives, for example, information including the error contents and the capsule ID of an error capsule from the workstation 8 belonging to the user A2 via the communication network 6, the central server 7 determines that an error about a capsule endoscope is notified (Yes at Step S108), and extracts the capsule IDs related to the error capsule from the registered capsule IDs (Step S109). Here, the capsule IDs related to the error capsule mean the capsule IDs that identify the other capsule endoscopes in which an error similar to the error capsule may occur.

At Step S109, the central server 7 refers to the manufacturing history information about the capsule endoscopes that the central server 7 holds and manages, and extracts, from the capsule IDs registered as the capsule IDs related to the error capsule, the capsule IDs of other capsule endoscopes (other capsule endoscopes in which the similar error may occur) having manufacturing history similar or identical to the manufacturing history (component parts thereof such as a battery, the manufacturing LOT number, the manufacturing date and time, the manufacturing location, and the like) of the error capsule.

If the capsule ID of the error capsule extracted by the central server 7 matches the capsule ID notified by the workstation 4 (that is, the capsule ID of the capsule endoscope used in the capsule endoscope system 10), the central server 7 transmits to the workstation 4 the error information of the capsule endoscope corresponding to the error contents notified by the workstation 8 (Step S110). The error information transmitted by the central server 7 includes the error contents of the error capsule that the central server 7 acquires from the workstation 8 belonging to the user A2 and the capsule ID of the error capsule extracted by the central server 7 at Step S109 as described above.

If the central server 7 does not receive, via the communication network 6, information including the error contents and the capsule ID of the error capsule at Step S108, the central server 7 determines that an error of the capsule endoscopes has not been notified (No at Step S108), and repeats the procedure at Step S108.

In the meantime, after transmitting the capsule ID to the central server 7, the workstation 4 determines whether error information is sent from the central server 7 while waiting for input of various data about the capsule endoscopes (such as the error contents and the capsule IDs) or the in-vivo images of the subjects (Step S111). More specifically, if the central server 7 transmits error information to the workstation 4 at Step S110, the communication unit 24 receives the error information from the central server 7 via the communication network 6. Then the communication unit 24 sends out to the control unit 26 the error information thus received. If the communication unit 24 receives error information from the central server 7, the control unit 26 determines that there is error information of the capsule endoscopes. If the communication unit 24 does not receive error information from the central server 7, the control unit 26 determines that there is no error information of the capsule endoscopes.

If it is determined that there is no error information of the capsule endoscopes (No at Step S111), the workstation 4 repeats the procedure at Step S111. In contrast, if it is determined that there is error information of the capsule endoscopes (Yes at Step S111), the workstation 4 determines whether the error capsule included in the error information is an unused capsule endoscope (Step S112).

At Step S112, the information management unit 26a checks the capsule ID of the error capsule included in the error information against the capsule list 25c. The information management unit 26a determines that the error capsule is an unused capsule endoscope if the capsule ID of the error capsule matches any of the capsule IDs included in the capsule list 25c, and determines that the error capsule is a used capsule endoscope if the capsule ID of the error capsule does not match any of the capsule IDs included in the capsule list 25c.

If the workstation 4 determines that the error capsule is an unused capsule endoscope (Yes at Step S112), the workstation 4 performs a warning process of capsule use prohibition to prohibit the use of the unused capsule endoscope determined to be an error capsule (an example of a warning process about an error of a capsule endoscope) (Step S113).

At Step S113, the control unit 26 instructs the display unit 22 to display thereon warning information that the use of the unused capsule endoscope determined to be an error capsule is prohibited. Here, the display unit 22 displays, as the warning information to prohibit the use of the capsule, information such as the capsule ID and the model number of the unused capsule endoscope determined to be an error capsule, information indicating that an error may occur in the unused capsule endoscope, and information indicating that use of the unused capsule endoscope is prohibited.

In contrast, if the workstation 4 determines that the error capsule is a used capsule endoscope (No at Step S112), the workstation 4 performs a warning process inducing the revision of the examination data including the in-vivo images captured by the used capsule endoscope determined to be an error capsule (an example of a warning process about an error of a capsule endoscope) (Step S114).

At Step S114, the control unit 26 instructs the display unit 22 to display thereon warning information inducing the revision of the examination data including the in-vivo images captured by the used capsule endoscope determined to be an error capsule. Here, the display unit 22 displays thereon, as the warning information to induce revision of the examination data, information such as the capsule ID and the model number of the used capsule endoscope determined to be an error capsule, information such as the file name of the case datum associated with the used capsule endoscope, the patient information included in the case datum, information inducing the revision of the case datum, and information indicating that the used capsule endoscope is an error capsule.

At Step S114, the information extracting unit 26b may extract from the examination data set the examination data of the subject associated with the capsule ID of the used capsule endoscope, and the control unit 26 may instruct the display unit 22 to display thereon the examination data extracted by the information extracting unit 26b (such as the in-vivo images and the diagnostic report information of the subject) along with the warning information inducing the revision of the examination data.

After performing the warning process about an error of the capsule endoscope (that is, the procedure performed at Step S113 or Step S114), the workstation 4 returns to the procedure performed at Step S101 and repeats the procedures at and after Step S101, while waiting for input of various data about the capsule endoscope (such as the error contents and the capsule ID) and various data such as the in-vivo images of the subject.

Figure 4:
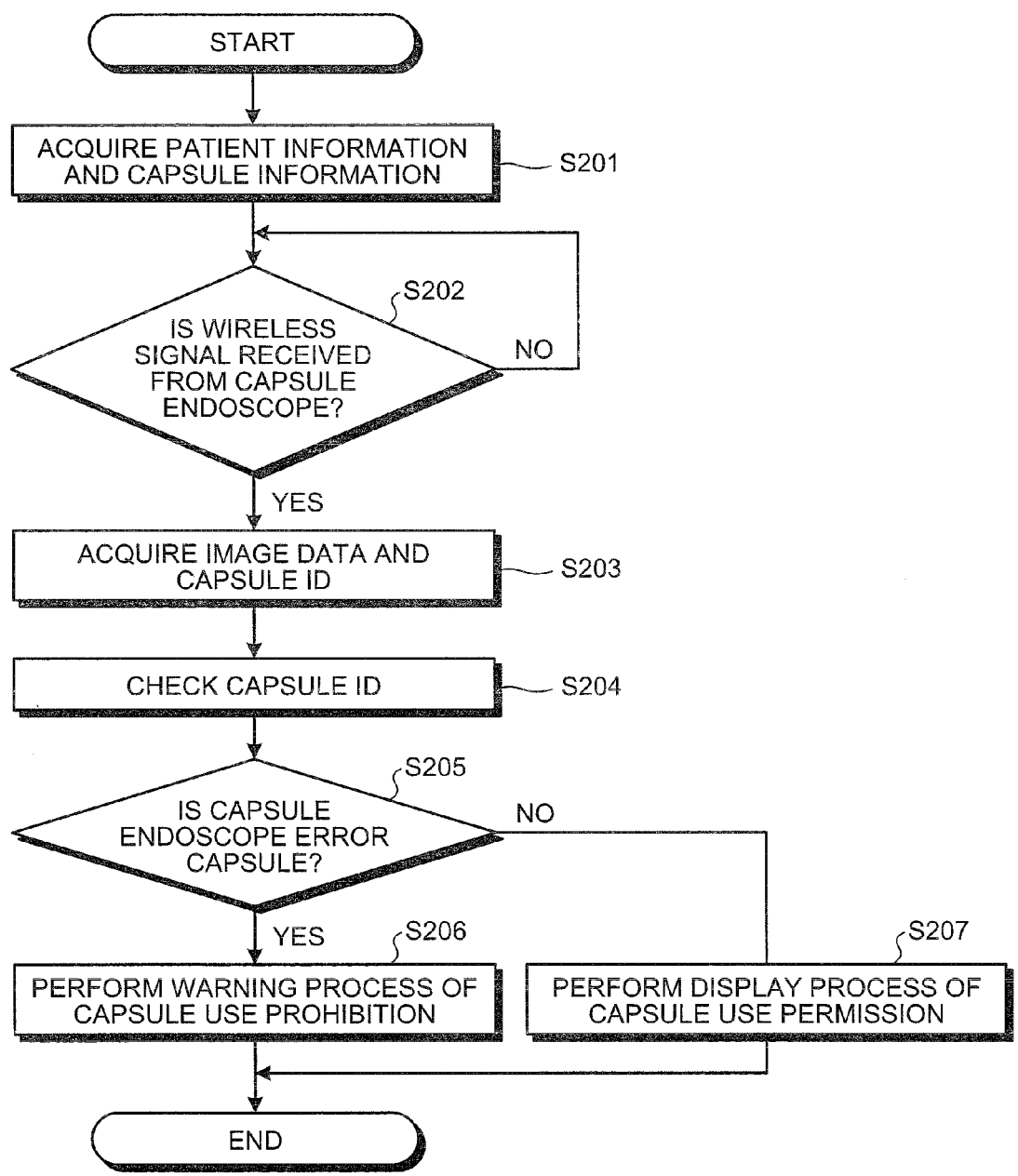
FIG. 4 is a flowchart showing an example of procedures performed by a receiving device that performs a warning process about an error of a capsule endoscope.

Procedures performed by the receiving device 3 of the capsule endoscope system 10 according to the first embodiment of the present invention are described below in detail. FIG. 4 is a flowchart showing an example of procedures performed by the receiving device 3 that performs a warning process about an error of a capsule endoscope. With an example of the receiving device 3 that is placed on (carried by) the subject 1 of which the capsule endoscope 2 is inserted into an organ, procedures performed by the receiving device 3 that performs a warning process about an error of a capsule endoscope are described below in detail.

As shown in FIG. 4, the receiving device 3 acquires from the workstation 4 through the recording medium 5, the patient information and the capsule information of the subject 1 of which the capsule endoscope 2 is inserted into an organ (Step S201). Here, the recording medium 5 in which the patient information and the capsule information of the subject 1 are recorded is inserted into the storage unit 15, and the control unit 16 acquires, from the recording medium 5 inserted into the storage unit 15, the patient information and the capsule information of the subject 1. In this way, the receiving device 3 is initially configured as a receiving device that receives the in-vivo images of the subject 1.

The capsule information recorded in the recording medium 5 includes the error capsule list created by the workstation 4 and the error contents of the error capsules identified by the capsule IDs included in the error capsule list.

The receiving device 3 determines whether a wireless signal is received from the capsule endoscope 2 to be inserted into an organ of the subject 1 (Step S202). More specifically, as an operation check, the capsule endoscope 2 captures an image on a trial basis and wirelessly transmits to the receiving device 3 the capsule ID and the image thus captured before being inserted into an organ of the subject 1. The receiving unit 11 receives the wireless signal transmitted by the capsule endoscope 2 on a trial basis, and transmits to the image processing unit 12 an image signal demodulated from the wireless signal. Then, the control unit 16 determines that a wireless signal is received from the capsule endoscope 2.

If the receiving unit 11 does not receive a wireless signal, the control unit 16 determines that no wireless signal is received from the capsule endoscope 2. If no wireless signal is received from the capsule endoscope 2 (No at Step S202), the receiving device 3 repeats the procedure at Step S202.

In contrast, if a wireless signal is received from the capsule endoscope 2 (Yes at Step S202), the receiving device 3 acquires the image data and the capsule ID included in the wireless signal from the capsule endoscope 2 (Step S203). More specifically, the receiving unit 11 demodulates the wireless signal received from the capsule endoscope 2 into an image signal as described above, and transmits the image signal to the image processing unit 12. The control unit 16 acquires from the image processing unit 12 the image data included in the image signal (that is, the image captured on a trial basis) and the capsule ID of the capsule endoscope 2.

Then, the receiving device 3 checks the capsule ID of the capsule endoscope 2 against the capsule IDs included in the error capsule list (Step S204), and then, determines whether the capsule endoscope 2 is an error capsule according to the check result (Step S205).

At Steps S204 and S205, the determination processing unit 16a checks the capsule ID of the capsule endoscope 2 against the error capsule list acquired at Step S201. If the capsule ID of the capsule endoscope 2 matches any one of the capsule IDs included in the error capsule list, the determination processing unit 16 determines that the capsule endoscope 2 is an error capsule. In contrast, if the capsule ID of the capsule endoscope 2 does not match any of the capsule IDs included in the error capsule list, the determination processing unit 16a determines that the capsule endoscope 2 is not an error capsule (that is, a normal capsule endoscope).

If the capsule endoscope 2 is determined to be an error capsule (Yes at Step S205), the receiving device 3 performs a warning process for capsule use prohibition to prohibit the use of the capsule endoscope 2 determined to be an error capsule (Step S206).

At Step S206, the control unit 16 instructs the display unit 14 to display thereon warning information indicating that the use of the capsule endoscope 2 determined to be an error capsule is prohibited. Here, the display unit 14 displays thereon, as the warning information of capsule use prohibition, information such as the capsule ID and the model number of the capsule endoscope 2 determined to be an error capsule, the contents of an error that may occur in the capsule endoscope 2 (that is, the capsule endoscope just before being inserted into an organ of the subject 1), and information indicating that the use of the capsule endoscope 2 is prohibited.

In contrast, if the capsule endoscope 2 is determined not to be an error capsule (No at Step S205), the receiving device 3 performs display operation of capsule use permission to permit the use of the capsule endoscope 2 determined to be normal (Step S207).

At Step S207, the control unit 16 instructs the display unit 14 to display thereon information indicating that the use of the capsule endoscope 2 determined to be normal is permitted. Here, the display unit 14 displays thereon information such as the capsule ID and the model number of the capsule endoscope 2 determined to be normal, information indicating that the capsule endoscope 2 (that is, the capsule endoscope just before being inserted into an organ of the subject 1) is normal, and information indicating that the use of the capsule endoscope 2 is permitted.

After performing the procedure performed at Steps S206 or S207, the receiving device 3 terminates the procedures while waiting for the wireless signal (the in-vivo images and the capsule ID of the subject 1) to be received from the capsule endoscope 2.

Figure 5:
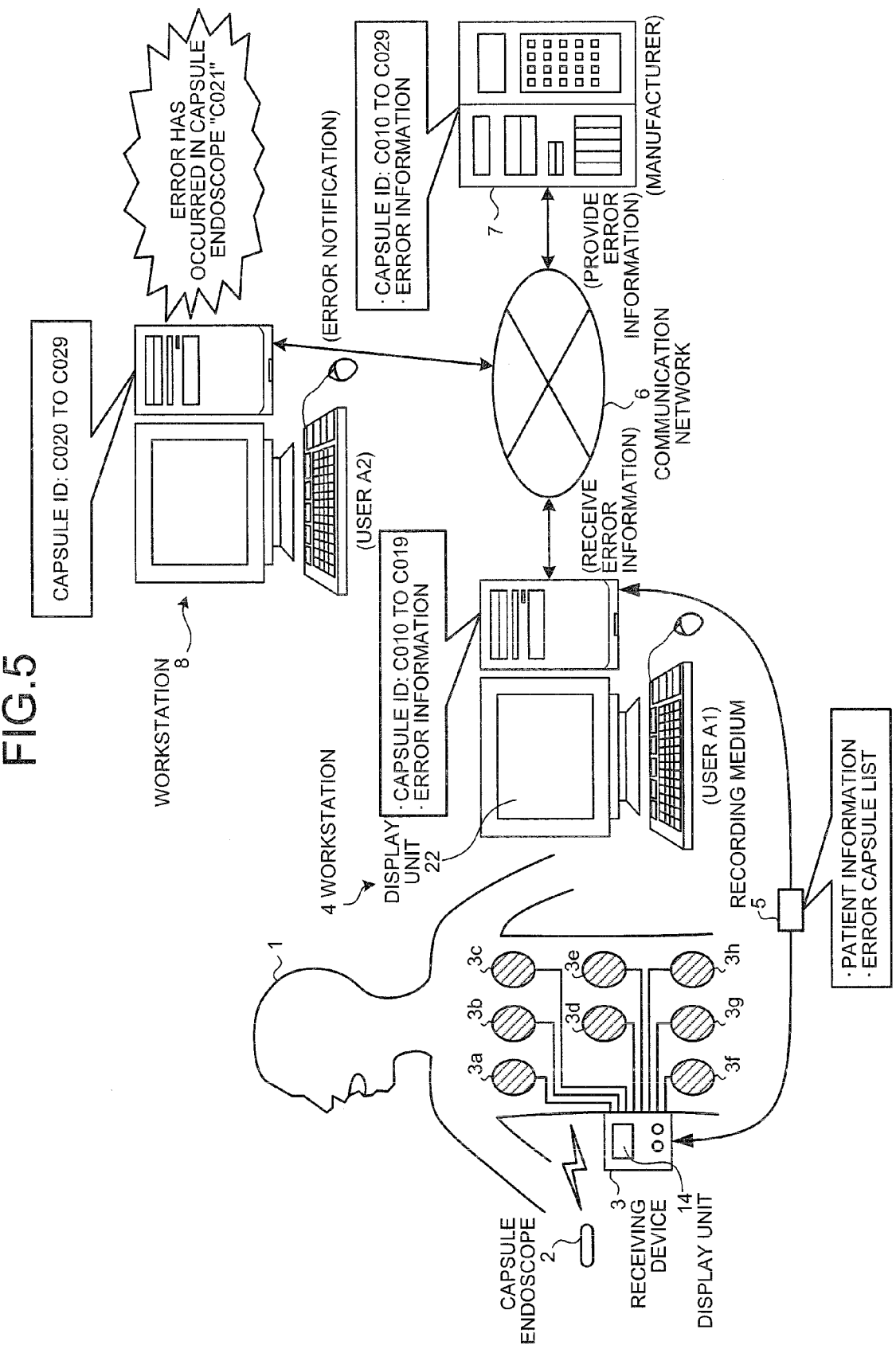
FIG. 5 is a schematic diagram specifically explaining operations performed by the workstation and the receiving device that perform a warning process about an error of a capsule endoscope.

Operations performed by the workstation 4 and the receiving device 3 in the capsule endoscope system 10 according to the first embodiment of the present invention are described below in detail. FIG. 5 is a schematic diagram specifically explaining operations performed by the workstation 4 and the receiving device 3 that perform a warning process about an error of a capsule endoscope.

As shown in FIG. 5, the workstation 4 acquires the capsule IDs (for example, ten capsule IDs "C010" to "C019") of plural capsule endoscopes used in the capsule endoscope system 10 belonging to the user A1 through the input operation performed with the input unit 21 and the like. The workstation 4 transmits to the central server 7 via the communication network 6, the ten capsule IDs "C010" to "C019" that the workstation 4 holds. In the meantime, the workstation 8 acquires the capsule IDs (for example, ten capsule IDs "C020" to "C029") of plural capsule endoscopes used in the capsule endoscope system (not shown) belonging to the user A2, and transmits to the ten capsule IDs "C020" to "C029" to the central server 7 via the communication network 6.

The central server 7 that belongs to the manufacturer receives via the communication network 6, the capsule IDs "C010" to "C019" from the workstation 4 and "C020" to "C029" from the workstation 8, and registers therein the 20 capsule IDs "C010" to "C029". The central server 7 transmits (provides) manufacturing history information of the ten capsule endoscopes identified by the capsule IDs "C010" to "C019" (that is, the capsule endoscopes used in the capsule endoscope system 10) to the workstation 4 belonging to the user A1. Similarly, the central server 7 transmits (provides) manufacturing history information of the ten capsule endoscopes identified by the capsule IDs "C020" to "C029" to the workstation 8 belonging to the user A2. Here, the workstation 4 receives from the central server 7 via the communication network 6, manufacturing history information of the ten capsule endoscopes identified by the capsule IDs "C010" to "C019". The workstation 8 receives from the central server 7 via the communication network 6, manufacturing history information of the ten capsule endoscopes identified by the capsule IDs "C020" to "C029".

If a battery exhaustion error in which the internal battery of a capsule endoscope is running out of power even though the capsule endoscope is within the expiration date of validity occurs in the capsule endoscope system belonging to the user A2, the workstation 8 notifies the central server 7 of the error contents of the battery exhaustion error and the capsule ID "C021" of the capsule endoscope in which the battery exhaustion is found. Then, the central server 7 receives from the workstation 8 via the communication network 6, the error contents of the battery exhaustion error and the capsule ID "C021" of the error capsule.

The central server 7 refers to manufacturing history information about the capsule endoscopes that the central server 7 holds and manages, and extracts from the registered capsule IDs the capsule ID "C011" of another capsule endoscope having manufacturing history identical or similar to the manufacturing history (component parts thereof such as a battery, the manufacturing LOT number, the manufacturing date and time, and the manufacturing location and the like) of the error capsule having the capsule ID "C021". The capsule endoscope having the capsule ID "C011" extracted by the central server 7 is a capsule endoscope in the capsule endoscope system belonging to the user A1, and a battery exhaustion error as in the error capsule having the capsule ID "C021" may occur therein. The central server 7 creates error information including the capsule ID "C011" thus extracted and the error contents of the battery exhaustion error, and transmits (provides) the error contents to the workstation 4 in the capsule endoscope system 10 that holds the capsule endoscope having the capsule ID "C011".

The workstation 4 receives via the communication network 6 the error information transmitted by the central server 7. Here, the workstation 4 checks the capsule ID "C011" included in the error information thus received against the capsule list 25c. Then, the workstation 4 determines whether the capsule endoscope identified by the capsule ID "C011" is unused according to the check result thus acquired. If the error capsule identified by the capsule ID "C011" is unused, the workstation 4 displays on the display unit 22 information such as the capsule ID "C011" and the model number of the unused error capsule, information indicating that a battery exhaustion error may occur in the unused error capsule even though the unused error capsule is within the expiration date of validity, and information indicating that the use of the unused error capsule is prohibited.

By having visual contact to the information displayed on the display unit 22, the user A1 can easily recognize that there is an error capsule in the unused capsule endoscopes. Then, the user A1 can exclude the capsule endoscope having the capsule ID "C011" as an error capsule. Thus, the user A1 can quickly deal with an error of a capsule endoscope. As a result, the user A1 can avoid inserting into the subject 1, the capsule endoscope in which battery exhaustion error may occur.

In contrast, if the error capsule identified by the capsule ID "C011" is used, the workstation 4 displays on the display unit 22 information such as the capsule ID "C011" and the model number of the used error capsule, information such as the file name of the case datum associated with the capsule ID "C011" of the used error capsule, the patient information included in the case datum, information inducing the revision of the case datum, and information indicating that the error capsule is used.

By having visual contact to the information displayed on the display unit 22, the user A1 can easily recognize that there is a case datum including the in-vivo images of the subject 1 captured by using the error capsule (that is, a defective case datum) in the examination data set. Then, the user A1 can quickly revise data such as the in-vivo images and the diagnostic result in the defective case datum. Therefore, the use A1 can quickly deal with an error of a capsule endoscope. As a result, if an error of a capsule endoscope occurs, a case datum that may have an error in the in-vivo images and the diagnostic result of the subject (that is, a defective case datum) can be quickly revised.

The receiving device 3 is placed on the subject 1 of which the capsule endoscope 2 is inserted into an organ. Then, the receiving device 3 acquires through the recording medium 5 the error capsule list created by the workstation 4 (including the capsule ID "C011") and the patient information of the subject 1. The receiving device 3 receives a wireless signal from the capsule endoscope 2 before the capsule endoscope 2 is inserted into an organ of the subject 1, and thus, acquires the image data captured by the capsule endoscope 2 on a trial basis and the capsule ID of the capsule endoscope 2.

The receiving device 3 checks the capsule ID "C011" included in the error capsule list against the capsule ID of the capsule endoscope 2. Thus, the receiving device 3 determines whether the capsule endoscope 2 is an error capsule. If the capsule ID of the capsule endoscope 2 is "C011", the receiving device 3 determines that the capsule endoscope 2 is an error capsule. Then, the receiving device 3 displays on the display unit 14 information such as the capsule ID and the model number of the capsule endoscope 2, information indicating that the capsule endoscope 2 is an error capsule (that is, battery exhaustion may occur in the capsule endoscope 2 even though the capsule endoscope 2 is within the expiration date of validity), and information indicating that the use of the capsule endoscope 2 is prohibited.

By having visual contact to the information displayed on the display unit 14, the user A1 can easily recognize that the capsule endoscope 2 just before being inserted into an organ of the subject 1 is an error capsule. Then, the user A1 can exclude the capsule endoscope 2 as an error capsule. Therefore, the user A1 can quickly deal with an error of a capsule endoscope. As a result, the user A1 can avoid inserting into the subject 1 the capsule endoscope 2 in which battery exhaustion error may occur.

In contrast, if the capsule ID of the capsule endoscope 2 is other than "C011", the receiving device 3 determines that the capsule endoscope 2 is normal. Here, the receiving device 3 displays on the display unit 14 information such as the capsule ID and the model number of the capsule endoscope 2 determined to be normal, information indicating that the capsule endoscope 2 is normal, and information indicating that the use of the capsule endoscope 2 is permitted.

By having visual contact to the information displayed on the display unit 14, the user A1 can easily recognize that the capsule endoscope 2 just before being inserted into an organ of the subject 1 is normal. Then, the capsule endoscope 2 determined to be normal can be safely inserted into an organ of the subject 1.

Figure 6:
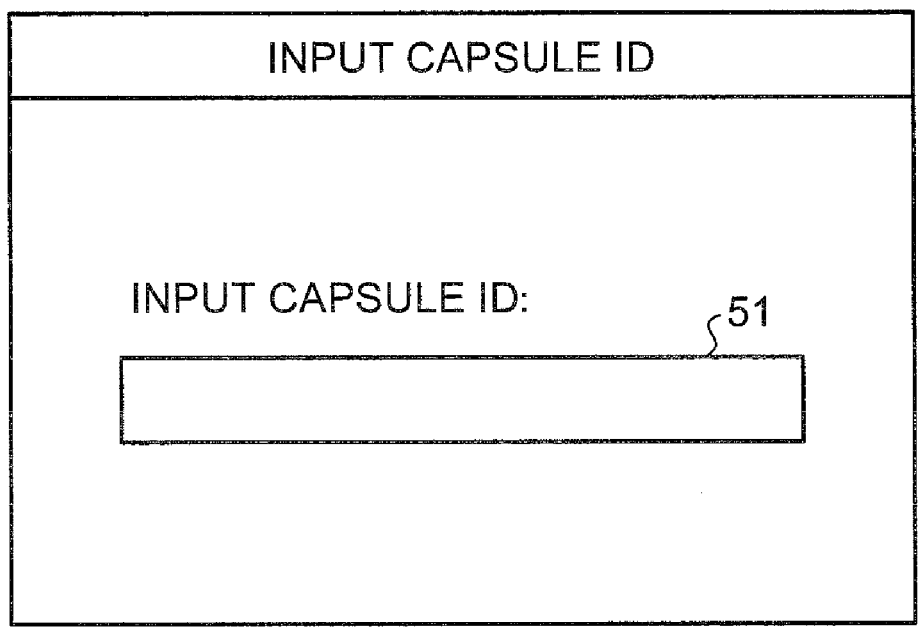
FIG. 6 is a schematic diagram showing an example of a window that is used for inputting a capsule ID.
Figure 7:
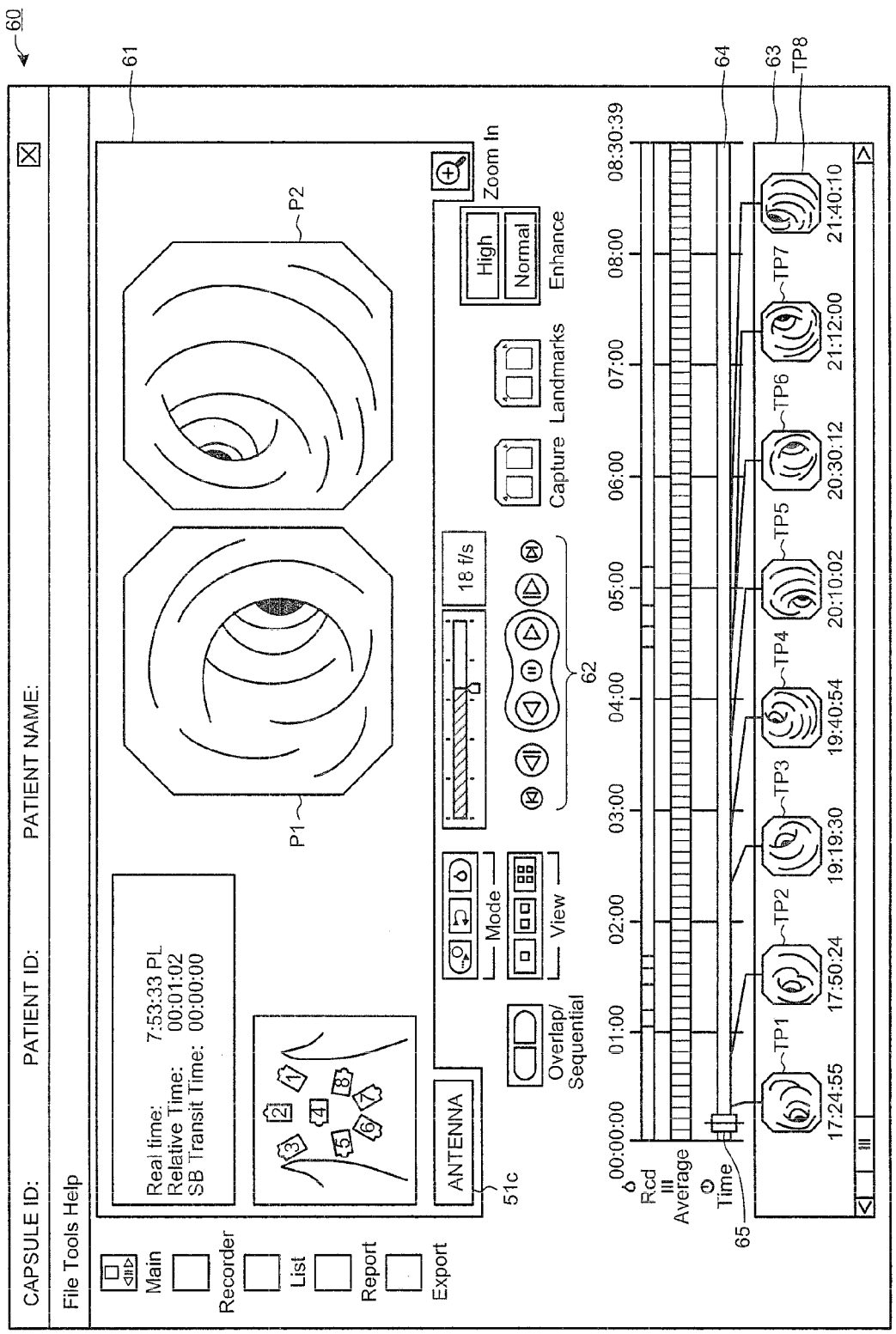
FIG. 7 is a schematic diagram showing an example of a window on which a case datum of a subject that corresponds to a capsule ID is displayed.

Operation performed by the control unit 26 when displaying on the display unit 22 in the workstation 4 the case datum of the subject (such as in-vivo images) associated with the capsule ID of a capsule endoscope is described below in detail. FIG. 6 is a schematic diagram showing an example of a window that is used for inputting a capsule ID. FIG. 7 is a schematic diagram showing an example of a window on which a case datum of the subject that corresponds to the capsule ID is displayed.

The control unit 26 instructs the display unit 22 to display thereon a window 50 as shown in FIG. 6 according to the instruction information input with the input unit 21. The window 50, which is a window used to input a capsule ID for extracting a desired case datum from the examination data set, has a text box 51 into which a capsule ID is input as shown in FIG. 6.

A desired capsule ID is input to the text box 51 according to input operation performed with the input unit 21. The input unit 21 inputs the capsule ID in the text box 51 to the control unit 26. The control unit 26 acquires the capsule ID input with the input unit 21 (that is, the desired capsule ID input to the text box 51). Here, the information extracting unit 26b extracts from the examination data set stored in the storage unit 25 the case datum of the subject 1 associated with the capsule ID.

The control unit 26 instructs the display unit 22 to display thereon the case datum of the subject 1 extracted by the information extracting unit 26b. Here, the control unit 26 instructs the display unit 22 to display thereon a window 60 on which the case datum of the subject 1 is displayed (see FIG. 7), instead of the window 50. The window 60 has a graphical user interface (GUI) used to observe the inside of an organ of the subject 1 by displaying thereon the in-vivo images (an example of case datum) of the subject 1. The control unit 26 controls display state of the window 60.

As shown in FIG. 7, the window 60 includes a main-image display section 61 on which an in-vivo image of the subject 1 is displayed, display operation icons 62 that are used to perform various display operations for displaying the in-vivo image on the main-image display section 61, and a sub-image display section 63 on which thumbnail images corresponding to desired in-vivo images selected from the in-vivo images of the subject 1 are displayed. The window 60 also includes a time bar 64 that indicates a time-position of each of the in-vivo images of the subject 1 and a slider 65 that indicates a time-position of the image currently displayed on the main-image display section 61. The capsule ID associated to the case datum of the images such as the in-vivo images displayed on the window 60 (that is, the capsule ID input to the text box 51 in the window 50) and the patient information of the subject 1 (for example, the patient ID and the patient name) in the case datum are displayed on the upper section of the window 60.

The in-vivo images of the subject 1 are successively displayed on the main-image display section 61 according to display operation with the display operation icons 62 (such as reproduce, fast-forward, and pause). The main-image display section 61 displays thereon one or more in-vivo images at once according to the setting of the number of images to be displayed thereon, as exemplified by in-vivo images P1 and P2 in FIG. 7. The main-image display section 61 displays thereon time information of an in-vivo image currently displayed thereon (that is, a currently displayed image). Time information displayed on the main-image display section 61 may include, for example, captured time of the currently displayed image and relative time of the in-vivo images of the subject 1 with respect to the forefront image (the in-vivo image having the earliest captured time).

The sub-image display section 63 displays thereon one or more thumbnail images corresponding to one or more in-vivo images selected from the in-vivo images displayed on the main-image display section 61. More specifically, when desired in-vivo images are successively selected from the in-vivo images displayed on the main-image display section 61, the thumbnail image corresponding to the desired in-vivo image (for example, the thumbnail images TP1 to TP8) are successively added to the thumbnail images upon each selection. The sub-image display section 63 has a scrolling function. Therefore, images that can be displayed on the sub-image display section 63 are not limited to the eight thumbnail images TP1 to TP8, and the desired number of thumbnail images can be displayed thereon.

The time bar 64 indicates time-position of each of the in-vivo images of the subject 1 displayed on the main-image display section 61. The slider 65 moves along the time bar 64 according to time information of a currently displayed image on the main-image display section 61, and thus, indicates time-position on the time bar 64 corresponding to the currently displayed image.

Figure 8:
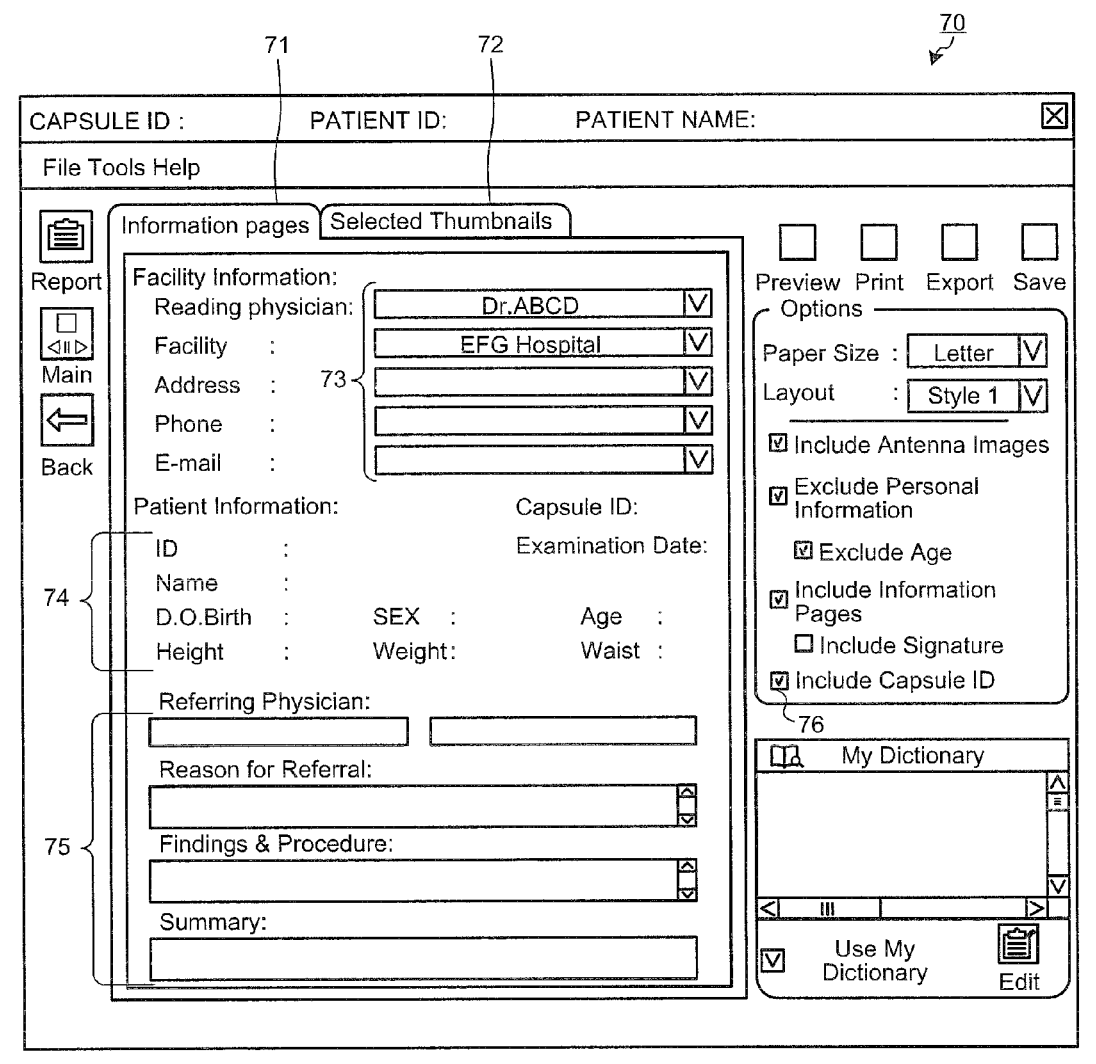

Operation performed by the report processing unit 26c that prepares a diagnostic report of the subject 1 is described below in detail. FIG. 8 is a schematic diagram showing an example of a window for preparing a diagnostic report of the subject 1. The control unit 26 instructs the display unit 22 to display thereon a window 70 as shown in FIG. 8 according to instruction information input with the input unit 21. The window 70 includes a GUI used for preparing a diagnostic report of the subject 1. The report processing unit 26c prepares a diagnostic report of the subject 1 according to information set by using the GUI of the window 70. The control unit 26 controls display state of the window 70.

As shown in FIG. 8, the window 70 includes an information page 71 on which various pieces of information included in the diagnostic report such as the diagnostic result of the subject 1 are edited and a thumbnail image page 72 on which images such as the thumbnail images contained in the diagnostic report of the subject 1 are examined. The window 70 includes a check box 76 for selecting whether the capsule ID of the capsule endoscope is to be included in the diagnostic report. The window 70 selectively displays thereon the information page 71 or the thumbnail image page 72.

As in the window 60, the capsule ID associated with the diagnostic report (an example of a case datum) (that is, the capsule ID input in the text box 51 on the window 50) and the patient information included in the case datum of the subject 1 (for example, the patient ID and the patient name) are displayed on the upper section of the window 70.

The information page 71 includes: text boxes 73 on which the name of the doctor (the name of the doctor who has diagnosed the subject 1) and the name of the institution (the name of the institution at which diagnosis is conducted on the subject 1), the address, the telephone number, and the email address that are to be included in the diagnostic report are set; an information display area 74 on which information such as the patient information, the examination information, and the capsule ID of the subject 1 is displayed; and text boxes 75, in which the name of the doctor at a referred facility, the reason for referral, the diagnostic result of the subject 1, and the summary of the diagnostic result are to be input.

The name of the doctor who has diagnosed the subject 1 and the name, the address, the telephone number, and the email address of the institution in which diagnosis is conducted are input in the text boxes 73 by operating the input unit 21. Information such as the patient information, the examination information, and the capsule ID of the subject 1 that the report processing unit 26c includes in the diagnostic report of the subject 1 is displayed on the information display area 74. Various pieces of information such as the name of the doctor at the referred facility, the reason for referral, the diagnostic result of the subject 1, and the summary are input in the text boxes 75 by operating the input unit 21.

The report processing unit 26c prepares the diagnostic report of the subject 1 associated with the capsule ID input in the text box 51 on the window 50 according to instruction information to prepare the diagnostic report input with the input unit 21. Here, the report processing unit 26c prepares the diagnostic report of the subject 1 with the various pieces of information input with the text boxes 73 and 75 and the case datum associated with the capsule ID. The contents of the diagnostic report prepared by the report processing unit 26c can be examined on the window 70 shown in FIG. 8 and the like.

According to the case datum of the subject 1 associated with the capsule ID, the report processing unit 26c includes on the diagnostic report of the subject 1, the patient information of the subject 1 (such as the patient ID, the patient name, the date of birth, the sex, the age, the height, the weight, and the waist size), the examination information of the subject 1 (such as the date on which the examination is conducted and the examination ID), and the capsule ID of the capsule endoscope 2 that captured the in-vivo images of the subject 1. In the report processing unit 26c, with operation such as clicking on a predetermined check box on the windows 70, whether personal data of the subject 1 (such as the date of birth, the sex, the age, the height, the weight, the waist size) and the capsule ID of the capsule endoscope 2 are to be included in the diagnostic report can be selected.

For example, if there is a check mark in the check box 76, the capsule ID of the capsule endoscope 2 is included in the diagnostic report of the subject 1, whereas when the no check mark is in the check box 76, the capsule ID of the capsule endoscope 2 is not included in the diagnostic report of the subject 1. The result of including the patient information, the examination information, and the capsule ID on the diagnostic report is displayed on the information display area 74 in the information page 71.

As described above, in the first embodiment of the present invention, a central server that uniformly manages various pieces of information about capsule endoscopes of plural users is connected via a communication network, the central server is notified of the held capsule IDs of one or more capsule endoscopes, information about the capsule endoscopes identified by the notified capsule IDs is acquired from the central server via the communication network, and a warning process about a capsule endoscope is performed according to the information acquired from the central server. Thus, if an error of a capsule endoscope is found by another user or by the capsule endoscope manufacturer, information about the error can be promptly acquired to perform a warning process about the capsule endoscope. As a result, the capsule endoscope system can be constructed in which the error of the capsule endoscope can be quickly be dealt with.

In the capsule endoscope system according to the first embodiment of the present invention, if there is an error capsule in the unused capsule endoscopes, the error capsule can be excluded before being used. As a result, inserting of a capsule endoscope in which a battery exhaustion error may occur into a subject can be prevented.

If there is an error capsule in the used capsule endoscopes, a case datum including in-vivo images of a subject captured by using the error capsule can be promptly found. As a result, a case datum that may have a defect in the in-vivo images and the diagnostic result of a subject can quickly be revised.

The central server uniformly manages held manufacturing history information of the capsule endoscopes. Therefore, manufacturing history information of one or more capsule endoscopes can easily be acquired therefrom via the communication network. Thus, manufacturing history information of a desired capsule endoscope can be easily displayed. As a result, manufacturing history information of a capsule endoscope can be confirmed at a desired timing.

As the capsule ID of a capsule endoscope capturing the in-vivo images of a subject associated with the case datum of the subject are held and managed, the capsule ID can easily be included in a diagnostic report prepared according to the case datum of the subject. Whether the capsule ID is to be included in a diagnostic report can be selected. Therefore, a diagnostic report on which the capsule ID is included and a diagnostic report on which the capsule ID is not included can be selectively prepared.

Second Embodiment

A second embodiment of the present invention is described below in detail. In the first embodiment, error information of a capsule endoscope is acquired from the central server, and then, the warning process of the error of the capsule endoscope is performed. In the second embodiment, information of the expiration date of validity of a capsule endoscope is further acquired from the central server, and then, a warning process about the expiration date of validity of the capsule endoscope is performed.

Figure 9:
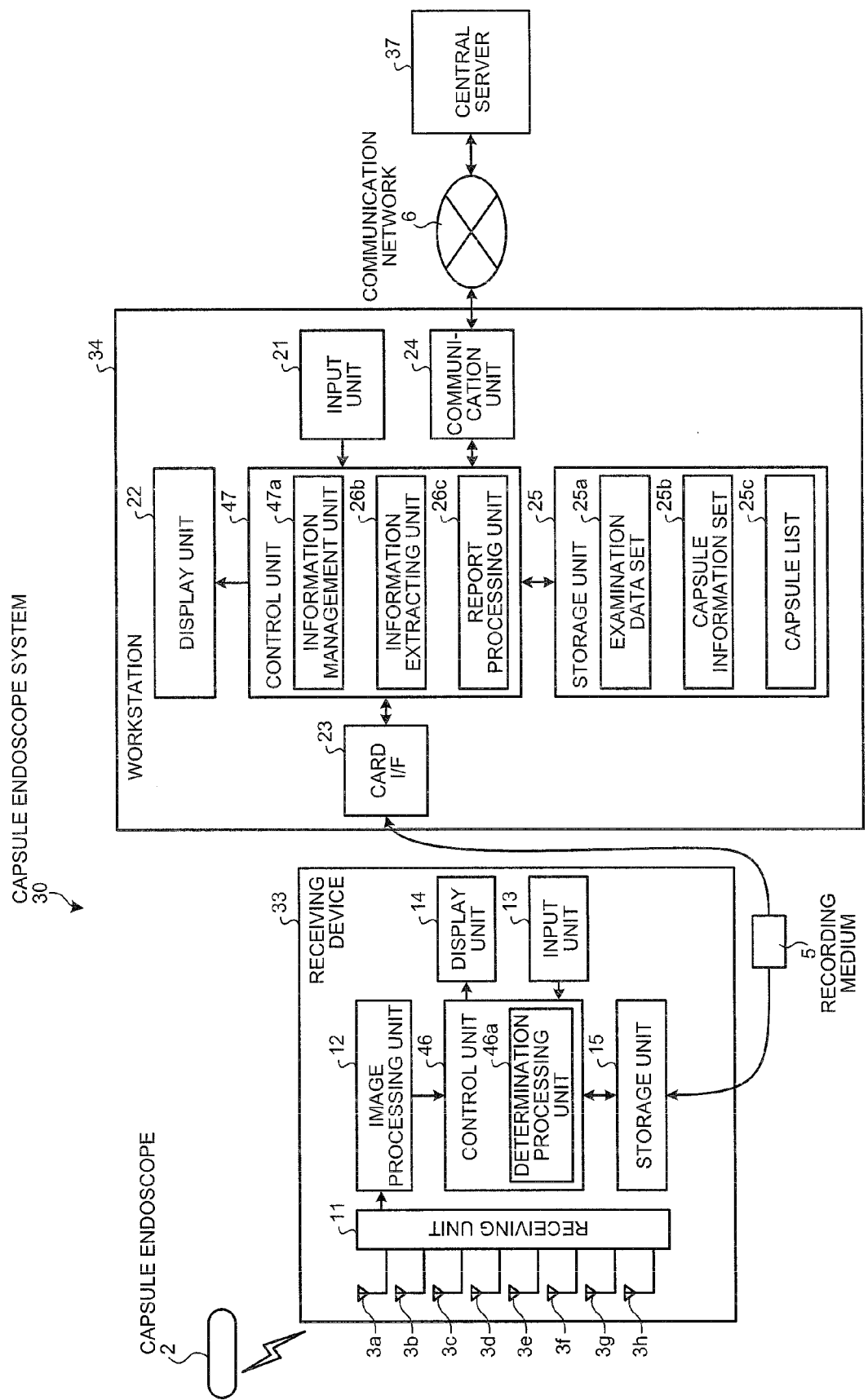
FIG. 9 is a block diagram schematically explaining a configuration example of a capsule endoscope system according to a second embodiment of the present invention.

FIG. 9 is a block diagram schematically explaining a configuration example of a capsule endoscope system according to the second embodiment of the present invention. As shown in FIG. 9, a capsule endoscope system 30 includes a receiving device 33 in place of the receiving device 3 in the capsule endoscope system 10 according to the first embodiment and a workstation 34 in place of the workstation 4. The receiving device 33 includes a control unit 46 in place of the control unit 16 in the receiving device 3 according to the first embodiment. The workstation 34 includes a control unit 47 in place of the control unit 26 in the workstation 4 according to the first embodiment, and is connected to a central server 37 in place of the central server 7. The central server 37 has a function similar to that of the central server 7 according to the first embodiment. Further, the central server 37 uniformly manages information of the expiration date of validity of plural endoscopes as information of capsule endoscopes of plural users (for example, the users A1 and A2). The central server 37 provides to a workstation of each user (for example, the workstations 8 and 34) via the communication network 6, the information of the expiration date of validity. The other configuration is the same as that of the first embodiment, and the same components are denoted by the same reference numerals.

The control unit 46 in the receiving device 33 determines whether the expiration date of validity (the expiration date for use) of the capsule endoscope 2 to be inserted into an organ of the subject 1 has already passed (hereinafter, referred to as an expired capsule). If the capsule endoscope 2 is determined to be an expired capsule, the control unit 46 instructs the display unit 14 to display thereon warning information warning externally that the capsule endoscope 2 is an expired capsule. The other functions performed by the control unit 46 are the same as that of the control unit 16 in the receiving device 3 according to the first embodiment.

The control unit 46 includes a determination processing unit 46a in place of the determination processing unit 16a in the receiving device 3 according to the first embodiment. The determination processing unit 46a has a determination processing function by which the determination processing unit 46a determines whether the capsule endoscope 2 is an error capsule, as in the determination processing unit 16a in the receiving device 3 according to the first embodiment. The determination processing unit 46a further has a determination processing function by which the determination processing unit 46a determines whether the capsule endoscope 2 is an expired capsule. When performing a determination process of an expired capsule, the determination processing unit 46a acquires through the recording medium 5 an expired capsule list created by the workstation 34. The determination processing unit 46a also acquires from the image processing unit 12 the capsule ID of the capsule endoscope 2 to be inserted into an organ of the subject 1. The capsule IDs of one or more expired capsules are listed in the expired capsule list. The determination processing unit 46a checks the capsule ID of the capsule endoscope 2 against the capsule IDs included in the expired capsule list, and determines whether the capsule endoscope 2 is an expired capsule, according to the check result. More specifically, the determination processing unit 46a determines that the capsule endoscope 2 is within the expiration date of validity if none of the capsule IDs in the expired capsule list match the capsule ID of the capsule endoscope 2, and determines that the capsule endoscope 2 is an expired capsule if any of the capsule IDs in the expired capsule list match the capsule ID of the capsule endoscope 2. If the determination processing unit 46a determines the capsule endoscope 2 to be an expired capsule, the control unit 46 instructs the display unit 14 to display thereon warning information indicating that the capsule endoscope 2 is an expired capsule.

Meanwhile, the control unit 47 in the workstation 34 controls the communication unit 24 to acquire from the central server 37 various pieces of information of the capsule endoscopes. Here, the control unit 47 also acquires, as the information about the capsule endoscopes, information of the expiration dates of the validity of the capsule endoscopes besides the error information and the manufacturing history information. The control unit 47 instructs the storage unit 25 to store therein the various pieces of information about the capsule endoscopes thus acquired, as a part of the capsule information set 25b. The control unit 47 may instruct the display unit 22 to display thereon the various pieces of information acquired from the central server 37 (such as the error information, the manufacturing history information, and the information about the expiration dates of validity). The control unit 47 instructs the display unit 22 to display thereon warning information of the expiration dates of validity of one or more capsule endoscopes, according to the information about the expiration dates of validity. The warning information about the expiration dates of validity of the capsule endoscopes may be, for example, warning information indicating that the validity of a capsule endoscope will expire in a predetermined period of time and warning information indicating that the expiration date of validity of a capsule endoscope has already passed. The other functions performed by the control unit 47 are similar to that of the control unit 26 in the workstation 4 according to the first embodiment.

The control unit 47 includes the information extracting unit 26b and the report processing unit 26c, and further includes an information management unit 47a in place of the information management unit 26a. The information management unit 47a further manages the information about the expiration dates of validity of the capsule endoscopes as information about the capsule endoscopes, besides the capsule IDs, the error information, and the manufacturing history information. The information management unit 47a associates one or more capsule IDs acquired from the input unit 21 or from the recording medium 5 inserted into the card I/F 23 with the various pieces of information included in the capsule information set 25b (such as the error information, the manufacturing history information, and the information about the expiration dates of validity). The information management unit 47a manages the error information, the manufacturing history information, and the information about the expiration dates of validity included in the capsule information set 25b for each capsule ID.

According to the information about the expiration dates of validity of the capsule endoscopes acquired from the central server 37 by operating the communication unit 24, the information management unit 47a creates an expired capsule list in which the capsule IDs of one or more expired capsules identified by the information about the expiration dates of validity are listed. The control unit 47 controls the card I/F 23 so that the expired capsule list created by the information management unit 47a is recorded in the recording medium 5. The other functions performed by the information management unit 47a are similar to that of the information management unit 26a in the workstation 4 according to the first embodiment.

The information about the expiration dates of validity that the control unit 47 acquires from the central server 37 via the communication network 6 includes the capsule ID of a capsule endoscope, the expiration date of validity of the capsule endoscope, and warning information indicating that the capsule endoscope is an expired capsule or that the validity of the capsule endoscope will be expired in a predetermined period of time.

Figure 10:
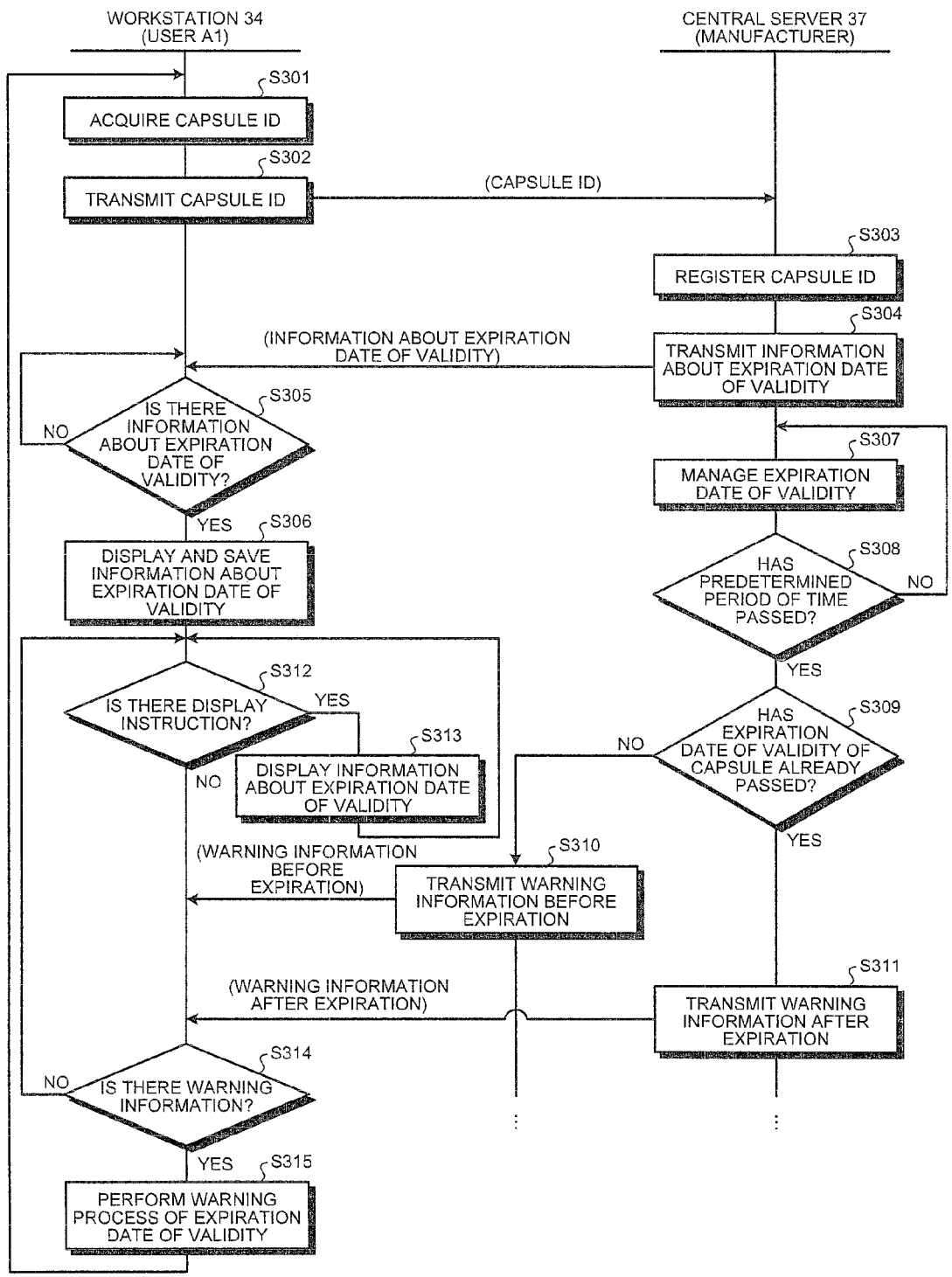
FIG. 10 is a sequence diagram showing an example of procedures performed by a workstation that performs a warning process about the expiration date of validity of a capsule endoscope.

Procedures performed by the workstation 34 in the capsule endoscope system 30 according to the second embodiment of the present invention are described below in detail. FIG. 10 is a sequence diagram showing an example of procedures performed by the workstation 34 that performs a warning process about the expiration date of validity of a capsule endoscope.

As shown in FIG. 10, similar to the procedures performed by the workstation 4 according to the first embodiment (Steps S101 and S102 shown in FIG. 3), the workstation 34 acquires the capsule ID of the capsule endoscope 2 used in the capsule endoscope system 30 belonging to the user A1 (Step S301), and transmits the capsule ID thus acquired to the central server 37 belonging to the manufacturer via the communication network 6 (Step S302).

The central server 37 receives the capsule ID from the workstation 34 via the communication network 6, and registers therein the capsule ID received from the workstation 34 (Step S303). Then, the central server 37 transmits to the workstation 34, the information about the expiration date of validity of the capsule endoscope identified by the capsule ID registered at Step S303 (that is, the capsule ID notified by the workstation 34) (Step S304). Then, the central server 37 may transmit to the workstation 34, the manufacturing history information of the capsule endoscope identified by the capsule ID notified by the workstation 34 along with the information about the expiration date of validity, although not specifically shown in FIG. 10.

Meanwhile, after transmitting the capsule ID to the central server 37, the workstation 34 determines whether information about the expiration date of validity from the central server 37 is available (Step S305), while waiting for input of various data such as various pieces of information about the capsule endoscopes and the in-vivo images of the subject. More specifically, if the central server 37 transmits the information about the expiration date of validity to the workstation 34 at Step S304, the communication unit 24 receives the information about the expiration date of validity from the central server 37 via the communication network 6, and then, sends out the information about the expiration date of validity to the control unit 47. The control unit 47 determines that information about the expiration date of validity is available if the communication unit 24 receives the information about the expiration date of validity from the central server 37, and determines that information about the expiration date of validity is not available if the communication unit 24 does not receive the information about the expiration date of validity from the central server 37.

If the workstation 34 determines that the information about the expiration date of validity is not available (No at Step S305), the workstation 34 repeats the procedure performed at Step S305. In contrast, if the workstation 34 determines that information about the expiration date of validity of the capsule endoscope is available (Yes at Step S305), the control unit 47 displays and saves the information about the expiration date of validity (Step S306). Here, the control unit 47 instructs the display unit 22 to display thereon the information about the expiration date of validity, and instructs the storage unit 25 to store therein the information about the expiration date of validity as a part of the capsule information set 25b. The information management unit 47a manages the information about the expiration date associated with the capsule ID.

Meanwhile, after transmitting the information about the expiration date of validity at Step S304, the central server 37 holds and manages various pieces of information about the capsule endoscopes (such as the capsule IDs and the manufacturing history information), and manages the expiration dates of validity of capsule endoscopes identified by the registered capsule IDs. Here, the central server 37 monitors, for example, whether the expiration date of validity of a capsule endoscope has already passed or whether there is any capsule endoscope in which the validity thereof will be expired in a predetermined period of time (for example, one to six months).

The central server 37 determines whether a predetermined period of time have passed after a capsule ID has been registered (Step S308). If the predetermined period of time has passed (Yes at Step S308), the central server 37 determines whether there is any expired capsule in the capsule endoscopes identified by the capsule IDs that are managed for the predetermined period after registration (Step S309).

The central server 37 refers to the expiration dates of validity of all the capsule endoscopes identified by the capsule IDs that are managed for the predetermined period of time after registration at Step S309. If the capsule endoscopes are within the expiration date of validity (No at Step S309), the central server 37 transmits to the workstation 34, warning information before expiration indicating that a predetermined period of time remains until the expiration date of validity of the capsule endoscope (Step S310). The warning information before expiration that the central server 37 transmits to the workstation 34 at Step S310 includes the capsule ID that the central server 37 acquired from the workstation 34 and information indicating that the validity of the capsule endoscope identified by the capsule ID is due in the predetermined period of time (for example, one to six months).

In contrast, the central server 37 refers to the expiration dates of validity of all the capsule endoscopes identified by the capsule IDs that are managed for the predetermined period of time after registration, and if the capsule endoscopes are expired capsule (Yes at Step S309), the central server 37 transmits to the workstation 34 warning information after expiration indicating that the expiration date of validity of the capsule endoscope has already passed (Step S311). The warning information after expiration that the central server 37 transmits to the workstation 34 at Step S311 includes the capsule ID that the central server 37 acquired from the workstation 34, information indicating that the expiration date of validity of the capsule endoscope identified by the capsule ID has already passed (that is, the capsule endoscope is an expired capsule), and information indicating the number of days that have passed after the expiration date of validity.

If the predetermined period of time has not passed after the capsule ID is registered at Step S308 (No at Step S308), the central server 37 returns to the procedure performed at Step S307, and repeats the procedures at and after Step S307.

Meanwhile, the workstation 34 determines whether there is a display instruction of the information about the expiration date of validity of the capsule endoscope after performing the procedure performed at Step S306 (Step S312). At Step S312, according to the user's needs, the input unit 21 is used to input to the control unit 47, the capsule ID and display instruction information of the expiration date of validity of a desired capsule endoscope of which confirmation of the expiration date of validity is desired. If the control unit 47 acquires the display instruction information and the capsule ID from the input unit 21, the control unit 47 determines that the information about the expiration date of validity is required to be displayed. If the control unit 47 does not acquire the display instruction information and the capsule ID from the input unit 21, the control unit 47 determines that there is no display instruction of the information about the expiration date of validity.

If the workstation 34 determines that there is display instruction of the information about the expiration date of validity (Yes at Step S312), the workstation 34 displays the information about the expiration date of validity of the capsule endoscope according to the display instruction (Step S313). Here, the control unit 47 instructs the display unit 22 to display thereon, the information about the expiration date of validity of the capsule endoscope identified by the capsule ID, according to the display instruction information and the capsule ID from the input unit 21. Then, the workstation 34 returns to Step S312, and repeats the procedures at and after Step S312.

In contrast, if the workstation 34 determines that there is no display instruction of the information about the expiration date of validity (No at Step S312), the workstation 34 determines whether there is a warning information about the expiration date of validity (Step S314), while waiting for input of various piece of information about the capsule endoscope (the error contents and the capsule IDs) or various data such as the in-vivo images of the subject.

More specifically, if the central server 37 transmits the warning information before expiration to the workstation 34 at Step S310, the communication unit 24 receives via the communication network 6, the warning information before expiration from the central server 37, and then, sends out the warning information before warning thus received to the control unit 47. If the central server 37 transmits the warning information after expiration to the workstation 34 at Step S311, the communication unit 24 receives via the communication network 6, the warning information after expiration, and then, sends out the warning information after expiration thus received to the control unit 47. If the communication unit 24 receives from the central server 37, the warning information before expiration or the warning information after expiration, the control unit 47 determines that there is warning information about the expiration date of validity of the capsule endoscope. If the communication unit 24 does not receive from the central server 37, the warning information before expiration or the warning information after expiration, the control unit 47 determines that there is no warning information about the expiration date of validity of the capsule endoscope.

If the workstation 34 determines that there is no warning information about the expiration date of validity of the capsule endoscope (No at Step S314), the workstation returns to Step S312, and repeats the procedures at Step S312. In contrast, if the workstation 34 determines that there is warning information about the expiration date of validity of the capsule endoscope (Yes at Step S314), the workstation 34 performs a warning process about the expiration date of validity of the capsule endoscope according to the warning information about the expiration date of validity (the warning information before expiration or the warning information after expiration) (Step S315).

If the warning information thus acquired is warning information before expiration, the control unit 47 instructs the display unit 22 to display thereon information warning that the validity of the capsule endoscope identified by the warning information before expiration is due in the predetermined period of time (for example, one to six months) at Step S315. If the warning information thus acquired is warning information after expiration, the control unit 47 instructs the display unit 22 to display thereon information warning that the expiration date of validity of the capsule endoscope identified by the warning information has already passed and information indicating the number of days that have passed after the expiration date of validity. In this manner, the workstation 34 accomplishes a warning process about the expiration date of validity of the capsule endoscope.

After performing the above described warning process about the expiration date of validity of the capsule endoscope (the procedure performed at Step S315), the workstation 34 returns to Step S301 and repeats the procedures at and after Step S301, while waiting for input of various data such as various pieces of information about the capsule endoscope (such as the error contents and the capsule IDs) and the in-vivo images of the subject.

Figure 11:
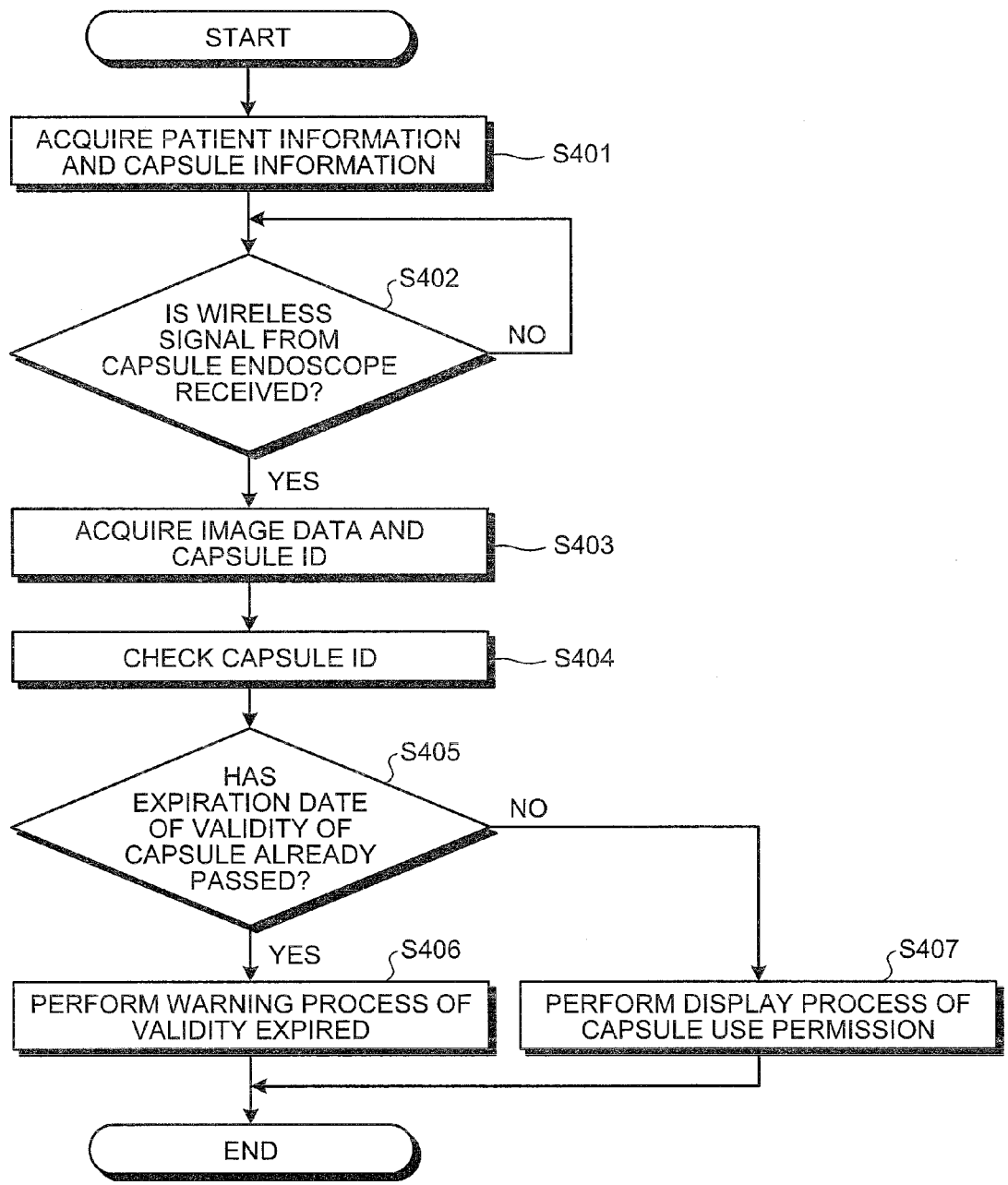
FIG. 11 is a flowchart showing an example of procedures performed by a receiving device that performs a warning process about the expiration date of validity of a capsule endoscope.

Procedures performed by the receiving device 33 in the capsule endoscope system 30 according to the second embodiment of the present invention are described below in detail. FIG. 11 is a flowchart showing an example of procedures performed by the receiving device 33 that performs the warning process about the expiration date of validity of a capsule endoscope. Below, with an example of the receiving device 33 that is placed on (carried by) the subject 1 of which the capsule endoscope 2 is to be inserted into an organ, procedures performed by the receiving device 33 that performs a warning process about the expiration date of validity of a capsule endoscope are described in detail.

As shown in FIG. 11, the receiving device 33 acquires from the workstation 34 through the recording medium 5, the patient information and the capsule information of the subject 1 of which the capsule endoscope 2 is to be inserted into an organ (Step S401). Here, the recording medium 5 in which the patient information and the capsule information of the subject 1 are recorded is inserted into the storage unit 15, and the control unit 46 acquires from the recording medium 5 inserted into the storage unit 15, the patient information and the capsule information of the subject 1. In this way, the receiving device 33 is initially configured as a receiving device that receives the in-vivo images of the subject 1.

The capsule information recorded in the recording medium 5 includes the expired capsule list created by the workstation 34 and the number of days that have passed after the expiration date of each expired capsule identified by each capsule ID listed in the expired capsule list, besides the error list and the error contents of the error capsules.

Similar to the procedures performed by the receiving device 3 (Steps S202 and S203 shown in FIG. 4) according to the first embodiment of the present invention, the receiving device 33 determines whether a wireless signal from the capsule endoscope 2 that is to be inserted into an organ of the subject 1 is received (Step S402). If the wireless signal is received (Yes at Step S402), the receiving device 33 acquires the image data and the capsule ID included in the wireless signal from the capsule endoscope 2 (Step S403). If the wireless signal is not received (No at Step S402), the receiving device 33 repeats the procedure at Step S402.

Then, the receiving device 33 checks the capsule ID of the capsule endoscope 2 acquired at Step S403 against the capsule IDs included in the expired capsule list (Step S404). The receiving device 33 determines whether the capsule endoscope 2 is an expired capsule, according to the check result.

At Steps S404 and S405, the determination processing unit 46*a* checks the capsule ID of the capsule endoscope 2 against the expired capsule list acquired at Step S401. If the capsule ID of the capsule endoscope 2 matches any of the capsule IDs included in the expired capsule list, the determination processing unit 46*a* determines that the capsule endoscope 2 is an expired capsule. In contrast, if the capsule ID of the capsule endoscope 2 does not match any of the capsule IDs included in the expired capsule list, the determination processing unit 46*a* determines that the capsule endoscope 2 is not an expired capsule (that is, the capsule endoscope 2 is within the expiration date of validity).

If the receiving device 33 determines that the capsule endoscope 2 is an expired capsule (Yes at Step S405), the receiving device 33 performs a warning process of the validity expiration warning that the capsule endoscope 2 is an expired capsule (Step S406).

At Step S406, the control unit 46 instructs the display unit 14 to display thereon warning information that the expiration date of validity of the capsule endoscope 2 has already passed. Then, the display unit 14 displays thereon information indicating that the capsule endoscope 2 is an expired capsule, information such as the capsule ID and the model number of the capsule endoscope 2 determined to be an expired capsule, and the number of days that have passed after the expiration date of validity of the capsule endoscope 2, as the warning information indicating that the expiration date of validity has already passed.

In contrast, if the receiving device 33 determines that the capsule endoscope 2 is not an expired capsule (No at Step S405), the receiving device 33 performs display operation of capsule use permission to permit the use of the capsule endoscope 2 that is within the expiration date of validity (Step S407).

At Step S407, the control unit 46 instructs the display unit 14 to display thereon information that the use of the capsule endoscope 2 that is determined to be within the expiration date of validity is permitted. Then, the display unit 14 displays thereon information such as the capsule ID and the model number of the capsule endoscope 2 that is within the expiration date of validity, information indicating that the capsule endoscope 2 (that is, the capsule endoscope just before being inserted into an organ of the subject 1) is within the expiration date, and information indicating that the use of the capsule endoscope 2 is permitted.

After performing the procedure performed at Step S406 or S407, the receiving device 33 terminates the procedures while waiting for the wireless signal (the in-vivo images and the capsule ID of the subject 1) to be received from the capsule endoscope 2. The receiving device 33 may perform the procedures performed at Steps S201 to S207 (see FIG. 4) described above to perform a warning process about an error of the capsule endoscope 2, in addition to performing the procedures at Steps S401 to S407 for a warning process about the expiration date of validity of the capsule endoscope 2.

Figure 12:
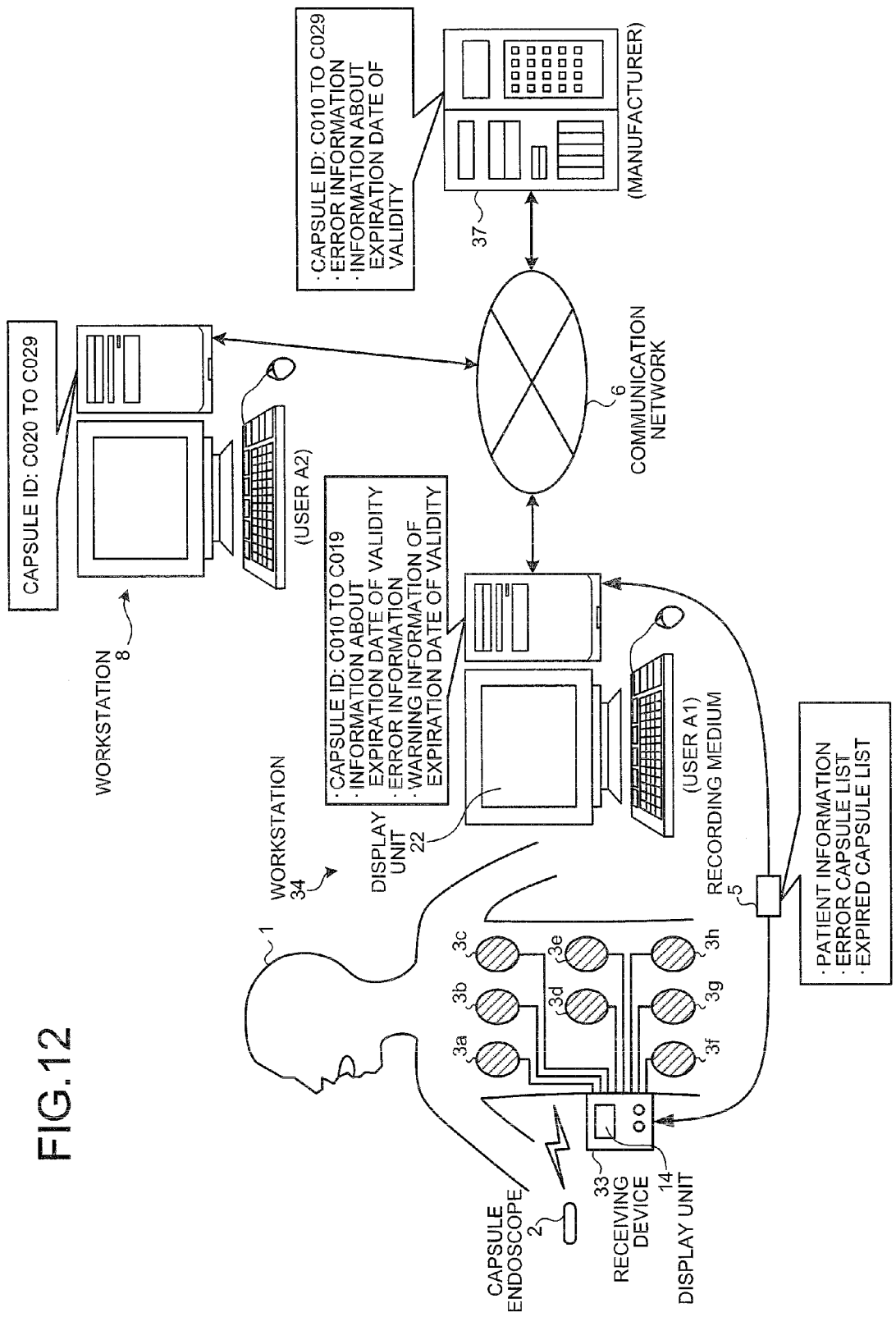
FIG. 12 is a schematic diagram specifically explaining operations performed by the workstation and the receiving device that perform a warning process about the expiration date of validity of a capsule endoscope.

Operations performed by the workstation 34 and the receiving device 33 in the capsule endoscope system 30 according to the second embodiment of the present invention are described below in detail. FIG. 12 is a schematic diagram specifically explaining operations performed by the workstation 34 and the receiving device 33 that perform a warning process about the expiration date of validity of a capsule endoscope.

As shown in FIG. 12, similar to the workstation 4 according to the first embodiment, the workstation 34 acquires the capsule IDs of plural capsule endoscopes used in the capsule endoscope system 30 (for example, the ten capsule IDs "C010" to "C019"), and transmits the ten capsule IDs "C010" to "C019" to the central server 37 via the communication network 6.

The central server 37 that belongs to the manufacturer receives via the communication network 6, the capsule IDs "C010" to "C019", and registers the ten capsule IDs "C010" to "C019" therein. The central server 37 separately receives from the workstation 8 belonging to the user A2, the capsule IDs "C020" to "C029" via the communication network 6. As a result, the central server 37 registers the 20 capsule IDs "C010" to "C029" therein.

The central server 37 transmits (provides) manufacturing history information and information about the expiration dates of validity of the ten capsule endoscopes identified by the capsule IDs "C010" to "C019" (that is, the capsule endoscopes used in the capsule endoscope system 30) to the workstation 34 belonging to the user A1. Similarly, the central server 37 transmits (provides) manufacturing history information and information about the expiration dates of validity of the ten capsule endoscopes identified by the capsule IDs "C020" to "C029" to the workstation 8 belonging to the user A2.

The workstation 34 receives from the central server 37 via the communication network 6, manufacturing history information and information about the expiration dates of validity of the ten capsule endoscopes identified by the capsule IDs "C010" to "C019", and then, holds and manages the manufacturing history information associated with the information about the expiration dates of validity thus received. Each time the workstation 34 receives from the central server 37, the manufacturing history information and the information about the expiration dates of validity, or each time the workstation 34 receives display instruction by operating the input unit 21, the workstation 34 displays the manufacturing history information and the information about the expiration dates of validity on the display unit 22.

If the central server 37 transmits to the workstation 34, warning information about the expiration date of validity of the capsule endoscope having the capsule ID "C012", the workstation 34 receives the warning information about the expiration date of validity from the central server 37. Then, the workstation 34 performs a warning process about the expiration date of validity of the capsule endoscope having the capsule ID "C012" according to the warning information of the expiration date of validity thus received. More specifically, if the warning information about the expiration date of validity is warning information before expiration, the workstation 34 displays on the display unit 22, information warning that the validity of the capsule endoscope identified by the capsule ID "C012" included in the warning information before expiration is due in the predetermined period of time (for example, one to six months).

As the user A1 has visual contact to the information displayed on the display unit 22, the user A1 can easily recognize that there is a capsule endoscope of which the validity expires in a predetermined period of time in the capsule endoscopes belonging to the user A1. Therefore, the user A1 can preferentially use the capsule endoscope of which the expiration date of validity is close. Thus, the user A1 can quickly respond to the expiration date of validity of a capsule endoscope. As a result, the user A1 can efficiently utilize a capsule endoscope within the expiration date of validity.

In contrast, if the warning information of the expiration date of validity acquired from the central server 37 is warning information after expiration, the workstation 34 displays on the display unit 22 information warning indicating that the capsule endoscope identified by the capsule ID "C012" included in the warning information after expiration is an expired capsule and information indicating the number of days that have passed after the expiration date of validity of the capsule endoscope.

As the user A1 has visual contact to the information displayed on the display unit 22, the user A1 can easily recognize that there is a capsule endoscope of which the expiration date of validity has already passed (that is, an expired capsule) in the capsule endoscopes belonging to the user A1, and can also easily recognize the number of days that have passed after the expiration date of validity of the expired capsule. If the expiration date of validity of a capsule endoscope defines the validity period of an internal battery of the capsule endoscope (that is, a period during which a battery can provide enough power), battery in the expired capsule exhausts faster than that in a capsule endoscope within the expiration date of validity. An expired capsule is, however, harmless to a human body. Therefore, the user A1 can use an expired capsule of which a battery life is shorter than a normal capsule endoscope according to different purposes of capsule endoscope examination (such as an esophagus examination and a stomach examination). For example, such an expired capsule can be used as a capsule endoscope for capturing in-vivo images of an esophagus or a stomach of which examination can be conducted in a relatively short period of time. As described above, the user A1 can quickly respond to the expiration of a capsule endoscope. As a result, such an expired capsule can be efficiently utilized according to different purposes.

Further, if the warning information of the expiration date of validity acquired from the central server 37 is warning information after expiration, the workstation 34 may display on the display unit 22 information indicating that the capsule endoscope identified by the capsule ID "C012" included in the warning information after expiration is an expired capsule and information indicating that the use of the expired capsule is prohibited. Then, the user A1 visually recognizes the information displayed on the display unit 22, and thus, can easily exclude the expired capsule. As a result, inserting an expired capsule into an organ of the subject can be prevented.

Meanwhile, the receiving device 33 is placed on the subject 1 of which the capsule endoscope 2 is inserted into an organ. Here, the receiving device 33 acquires through the recording medium 5, the error capsule list created by the workstation 34, the expired capsule list (including the capsule ID "C012"), information of the number of days that have passed after the expiration date, and the patient information of the subject 1. The receiving device 33 receives a wireless signal from the capsule endoscope 2 before the capsule endoscope 2 is inserted into an organ of the subject 1, and thus, acquires the capsule ID of the capsule endoscope 2 as well as the image data captured by the capsule endoscope 2 on a trial basis.

The receiving device 33 checks the capsule ID "C012" included in the expired capsule list against the capsule ID of the capsule endoscope 2 and determines whether the capsule endoscope 2 is an expired capsule. If the capsule ID of the capsule endoscope 2 is "C012", the receiving device 33 determines that the capsule endoscope 2 is an expired capsule. Here, the receiving device 33 displays on the display unit 14, information such as the capsule ID and the model number of the capsule endoscope 2, information indicating that the capsule endoscope 2 is an expired capsule, and information indicating the number of days that have passed after the expiration date of validity of the capsule endoscope 2.

As the user A1 has visual contact to the information displayed on the display unit 14, the user A1 can easily recognize that the capsule endoscope 2 just before being inserted into an organ of the subject 1 is an expired capsule. The user A1 can also easily recognize the number of days that have passed after the expiration date of the capsule endoscope 2. Thus, the user A1 can decide a use of the capsule endoscope 2 (that is, an expired capsule) according to the number of days that have passed after the expiration date of the capsule endoscope 2. The user A1 may use the capsule endoscope 2 as a capsule endoscope that specifically captures an in-vivo image of an esophagus or a stomach of which examination can be conducted in a relatively short period of time. The user A1 may also exclude the capsule endoscope 2 that is an expired capsule instead of inserting the capsule endoscope 2 into an organ of the subject 1. Thus, the user A1 can quickly deal with the expiration of a capsule endoscope. As a result, an expired capsule can be utilized efficiently according to different purposes, and inserting of such an expired capsule into the subject 1 can be prevented.

If the capsule endoscope 2 is an expired capsule, the receiving device 33 may display on the display unit 14 information such as the capsule ID and the model number of the capsule endoscope 2, information indicating that the capsule endoscope 2 is an expired capsule, information indicting the number of days that have passed after the expiration date of validity of the capsule endoscope 2, and information indicating that the use of the capsule endoscope 2 is prohibited.

In contrast, if the capsule ID of the capsule endoscope 2 is other than "C012", the receiving device 33 determines that the capsule endoscope 2 is within the expiration date of validity. Thus, the receiving device 33 displays on the display unit 14 information such as the capsule ID and the model number of the capsule endoscope 2, information indicating that the capsule endoscope 2 is within the expiration date of validity, and information indicating that the use of the capsule endoscope 2 is permitted.

As the user A1 has visual contact to the information displayed on the display unit 14, the user A1 can easily recognize that the capsule endoscope 2 just before being inserted into an organ of the subject 1 is within the expiration date of validity. Thus, the user A1 can safely insert the capsule endoscope 2 within the expiration date of validity into an organ of the subject 1.

As described above, in the second embodiment of the present invention, information about the expiration date of validity of a capsule endoscope, as information about the capsule endoscope, is further acquired from a central server that uniformly manages various pieces of information about plural capsule endoscopes, a warning process about the expiration date of validity of the capsule endoscope is performed according to the information about the expiration date of validity thus acquired, and other elements are configured to be similar to that of the first embodiment. Thus, the warning process about an error of a capsule endoscope can be quickly performed. The expiration dates of validity of the capsule endoscopes belonging to the user can be easily examined. Further, a warning process about the expiration date of validity of the capsule endoscope can be quickly performed. As a result, a capsule endoscope system can be formed in which the effects of the first embodiment can be acquired and in which the expiration date of validity of a capsule endoscope can be quickly dealt with.

In the capsule endoscope system according to the second embodiment of the present invention, an expired capsule can be utilized according to different uses in capsule endoscope examination. As a result, an expired capsule can be utilized efficiently. An expired capsule can be excluded before being used. As a result, inserting of an expired capsule into a subject can be prevented.

According to the first and the second embodiments of the present invention, the workstations 4 and 34 each acquire a capsule ID recorded in the recording medium 5 with the image data or acquire a capsule ID input with the input unit 21. The present invention is, however, not limited thereto. An optical mark reader such as a CCD and CMOS image sensors may be further provided to the workstations 4 and 34, and a capsule ID on a casing or a package of a capsule endoscope may be optically read by using the optical mark reader. Then, workstations 4 and 34 may acquire the capsule ID thus optically read. The capsule ID optically read by using the optical mark reader may be formed of dots, bars, and the like, or may be formed by combination of characters, alphanumeric characters, and the like.

In the first and the second embodiments of the present invention, workstations of the two users A1 and A2 and the central server that belongs to the manufacturer are connected to each other via the communication network 6. The present invention is, however, not limited thereto. The central server that belongs to the manufacturer can be connected to the workstations that belong to three or more users via the communication network 6. The central server may provide various pieces of information about the capsule endoscopes to the workstations belonging to three or more users.

In the first and the second embodiments of the present invention, the central server that belongs to the manufacturer transmits to the workstations of the users via the communication network 6, various pieces of information about the capsule endoscopes. The present invention is, however, not limited thereto. The workstations of the users may transmit to the central server that belongs to the manufacturer via the communication network 6, operation LOG information of a capsule endoscope or a workstation, facility information (that is, information about a facility such as a hospital in which a capsule endoscope system is adopted) that are associated with each capsule ID. The operation LOG information or the facility information acquired by the central server that belongs to the manufacturer can be utilized for product development of a future capsule endoscope system (such as a capsule endoscope, a receiving device, and a workstation).

In the first and the second embodiments of the present invention, if the capsule endoscope 2 to be inserted into an organ of the subject 1 is an error capsule or an expired capsule, warning information is displayed on the display unit 14 in the receiving device 3 or 33. The present invention is, however, not limited thereto. If the capsule endoscope 2 is an error capsule or an expired capsule, receiving of a wireless signal from the capsule endoscope 2 may be cancelled so that the receiving device 3 or 33 receive no image data from the capsule endoscope 2.

According to the first and the second embodiments of the present invention, information such as the patient information, the diagnostic result, the examination information, and the capsule ID of the subject 1 is included in the diagnostic report. The present invention is, however, not limited thereto. The manufacturing history information of the capsule endoscope may further be included in the diagnostic report.

In the first and the second embodiments of the present invention, information about an error and the expiration date of validity of a capsule endoscope is displayed on the display unit 22 in the workstations 4 and 34 and on the display unit 14 in the receiving devices 3 and 33. The present invention is, however, not limited thereto. A use of a capsule endoscope (that is, information such as for esophagus examination, for stomach examination, for small intestine examination, for large intestine examination, and of a magnetic guiding capsule endoscope) associated with each capsule ID may further be displayed thereon.

In the second embodiment of the present invention, a warning process about the expiration date of validity of a capsule endoscope is further performed in addition to a warning process about an error of a capsule endoscope. The present invention is, however, not limited thereto. A warning process about the expiration date of validity of a capsule endoscope may be performed without performing a warning process about an error of a capsule endoscope.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule endoscope system comprising:
    a receiving device that receives in-vivo images captured by a capsule endoscope inserted into an organ of a subject;
    a storage unit that stores therein a list of ID information of unused capsule endoscopes; and
    an image display device that acquires ID information of one or more capsule endoscopes, acquires through the receiving device the in-vivo images captured by the capsule endoscopes identified by the ID information, and displays thereon the in-vivo images thus acquired, wherein
    the image display device is connected via a communication network to a central server that uniformly manages information about the capsule endoscopes, notifies the central server the ID information of the one or more capsule endoscopes, acquires information about the one or more capsule endoscopes from the central server, and performs a warning process about the one or more capsule endoscopes according to the information thus acquired, and
    the image display device performs the warning process about one of the capsule endoscopes before the one of the capsule endoscopes is used if the one of the capsule endoscopes is determined, based on the list stored in the storage unit, to be an unused capsule endoscope, and performs the warning process after the one of the capsule endoscopes is used if the one of the capsule endoscopes is determined, based on the list stored in the storage unit, to be a used capsule endoscope.

2. The capsule endoscope system according to claim 1, wherein
    the information about the one or more capsule endoscopes includes error information,
    the central server registers therein the ID information of the one or more capsule endoscopes notified by the image display device, and when the central server acquires via the communication network an error notification of another capsule endoscope related to the one or more capsule endoscopes, transmits to the image display device that has the registered ID information of the one or more capsule endoscopes the error information corresponding to the error notification of the another capsule endoscope, and
    the image display device acquires the error information via the communication network and performs the warning process about an error of the capsule endoscope corresponding to the error information.

3. The capsule endoscope system according to claim 2, wherein
    the image display device creates an ID information list of the capsule endoscopes identified by the error information, and
    the receiving device comprises:
        a receiving unit that receives the image captured by the capsule endoscope inserted into the organ of the subject and ID information of the capsule endoscope;
        a display unit that displays thereon warning information indicating that the capsule endoscope has the error; and
        a control unit that acquires the ID information list created by the image display device, checks the ID information of the capsule endoscope against the ID information list, determines whether the capsule endoscope has the error, and instructs the display unit to display thereon the warning information when the capsule endoscope is determined to have the error.

4. The capsule endoscope system according to claim 1, wherein
the information about the one or more capsule endoscopes includes information about expiration dates of validity,
the central server registers therein ID information of the one or more capsule endoscopes notified by the image display device, and transmits to the image display device that has the registered ID information of the one or more capsule endoscopes the information about the expiration dates of validity, and
the image display device acquires via the communication network the information about the expiration dates of validity, and performs the warning process about the expiration dates of validity of the capsule endoscopes corresponding to the information about the expiration dates of validity.

5. The capsule endoscope system according to claim 4, wherein the information about the expiration date of validity includes at least one of warning information before expiration indicating that the expiration date of validity of the capsule endoscope is due in a predetermined period of time and warning information after expiration indicating that the expiration date of validity of the capsule endoscope has already passed.

6. The capsule endoscope system according to claim 4, wherein
the image display device creates an ID information list of the capsule endoscopes whose expiration dates have already passed, which are identified by the information about the expiration dates of validity, and
the receiving device comprises:
a receiving unit that receives the image captured by the capsule endoscope inserted into the organ of the subject and ID information of the capsule endoscope;
a display unit that displays thereon warning information indicating that the expiration date of the capsule endoscope has already passed; and
a control unit that acquires the ID information list created by the image display device, checks the ID information of the capsule endoscope against the ID information list, determines whether the expiration date of the capsule endoscope has already passed, and instructs the display unit to display thereon the warning information when the expiration date of the capsule endoscope is determined to have already passed.

7. The capsule endoscope system according to claim 1, wherein the image display device comprises:
a display unit that displays thereon examination data of the subject including the in-vivo images captured by the capsule endoscope;
an information acquiring unit that acquires the ID information of the capsule endoscope; and
a control unit that manages the examination data of the subject with its associated ID information of the capsule endoscope, extracts the examination data of the subject according to the ID information of the capsule endoscope acquired by the information acquiring unit, and displays on the display unit the examination data of the subject thus extracted.

8. The capsule endoscope system according to claim 7, wherein the information acquiring unit acquires the in-vivo images of the subject and the ID information of the capsule endoscope through the receiving device.

9. The capsule endoscope system according to claim 7, wherein the information acquiring unit is an optical information reading unit that optically reads the ID information of the capsule endoscope.

10. The capsule endoscope system according to claim 7, wherein the information acquiring unit is an input unit that inputs the ID information of the capsule endoscope.

11. The capsule endoscope system according to claim 1, wherein the image display device comprises a report creating unit that creates a diagnostic report of the subject in which the ID information of the capsule endoscope is described.

12. The capsule endoscope system according to claim 11, wherein the report creating unit selects whether the ID information of the capsule endoscope is to be described in the diagnostic report of the subject.

* * * * *